(12) United States Patent
Kahne et al.

(10) Patent No.: US 6,413,732 B1
(45) Date of Patent: Jul. 2, 2002

(54) SUBSTRATE ANALOGS THAT SUBSTITUTE FOR LIPID I AS A SUBSTRATE FOR MURG

(75) Inventors: Suzanne Walker Kahne; Hongbin Men, both of Princeton; Peter Park, East Rutherford; Min Ge, Princeton, all of NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 09/241,862

(22) Filed: Feb. 2, 1999

Related U.S. Application Data

(60) Provisional application No. 60/073,376, filed on Feb. 2, 1998.

(51) Int. Cl.$^7$ .......................... C12Q 1/48; A61K 38/08
(52) U.S. Cl. .......................... 435/15; 514/17; 530/812
(58) Field of Search ....................... 435/24, 15; 514/17; 530/812

(56) References Cited

U.S. PATENT DOCUMENTS 5,153,173 A    10/1992  Suskovic et al. ............... 514/8
6,153,381 A  * 11/2000  Rothstein ....................... 435/6

OTHER PUBLICATIONS

Baker et al., Analytical Biochemistry, 239, 20–24, 1996.*
Gegnas et al. "Inhibitors of the Bacterial Cell Wall Biosynthesis Enzyme", MurD. Bioorg. Med. Chem. Lett. 1998, vol. 8, pp. 1643–1648.
Sharma et al. "Synthesis and Antitumor Activity of a Novel Muramic Acid Peptidoglycan Analog", In: Proc. Int. Cancer Congress, 16th Annual Meeting. Edited by: R. Rao., Bologna, Italy: Monuzzi Editore, 1994, vol. 16, pp. 491–494.
Pless et al., "Initial Membrane Reaction in Peptidoglycan Synthesis", J. Biol. Chem. 1973, vol. 248, No. 5, pp. 1568–1576.
Auger et al., "Synthesis of an Analogue of the Lipoglycopeptide Membrane Intermediate I of Peptidoglycan Biosynthesis", Lett. Peptide Sci., 1997, vol. 4, pp. 371–376.
L.A.J.M. Sliedregt, et al., "Trimethylsilyl Triflate Mediated Chemoselective Condensation of Arylsulfenyl Glycosides", Tetrahedron Letters, vol. 35, No. 23, 1994, pp. 4015–4018.
Suzanne Walker, et al., "Analysis of Hydroxylamine Glycosidic Linkages: Structural Consequences of the NO Bond in Calicheamicin", J. Am. Chem. Soc., vol. 116, No. 8, 1994, pp. 3197–3206.
Lin Yan, et al., "Glycosylation on the Merrifield Resin Using Anomeric Sulfoxides", J. Am. Chem. Soc., vol. 116, No. 15, 1994, pp. 6593–6954.
Frank Barresi, "Glycosylation Methods in Oligosaccharide Synthesis", Modern Synthetic Methods, 1995, pp. 283–328.

* cited by examiner

Primary Examiner—David M. Naff
Assistant Examiner—Mike Meller
(74) Attorney, Agent, or Firm—Woodcock Washburn LLP

(57) ABSTRACT

General methods for monitoring the activity of MurG, a GlcNAc transferase involved in bacterial cell wall biosynthesis, is disclosed. More particularly, the synthesis of simplified substrate analogs of Lipid I (the natural substrate for MurG), which function as acceptors for UDP-GlcNAc in an enzymatic reaction catalyzed by MurG, is described. Assays using the substrate analogs of the invention are further disclosed, which are useful for identifying a variety of other substrates, including inhibitors of MurG activity, for facilitating mechanistic and/or structural studies of the enzyme and for other uses. High throughput assays are also described.

10 Claims, 8 Drawing Sheets

Figure 1:
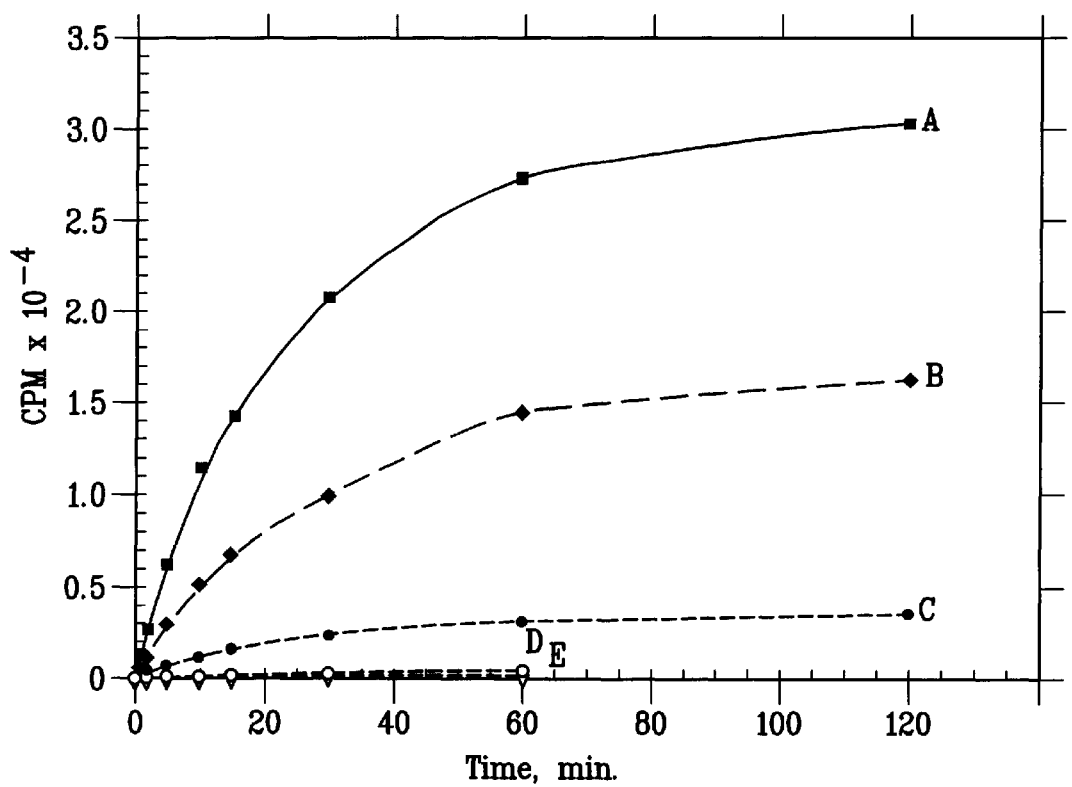

Initial Rate Data for wild-type MurG using synthetic substrate analog 1b.

Lipid I: R' = H    R'' =

1a: R' = H    R'' =

1b: R' =

14a: R = CH3
14b: R = CH3CH2
14c: R = CH2=CHCH2

SUBSTRATE ANALOGS THAT SUBSTITUTE FOR LIPID I AS A SUBSTRATE FOR MURG

RELATED APPLICATIONS

This application claims priority to U.S. Provisional Application Ser. No. 60/073,376, filed Feb. 2, 1998 the entire disclosure of which is incorporated by reference herein.

1. FIELD OF THE INVENTION

The present invention relates to substrate analogs of UDP-GlcNAc:muramyl pentapeptide pyrophosphoryl, N-acetylglucosaminyltransferase (GlCNAc transfer, MurG, or its homologs), an enzyme involved in a bacterial cell wall biosynthesis. The substrate analogs of the invention are useful as functional substitutes of Lipid I, the membrane bound, natural substrate of MurG. In particular, the substrate analogs of the present invention can be used advantageously in an assay for the enzymatic activity catalyzed by MurG, in methods for identifying other substrate analogs of MurG, as well as inhibitors of enzymatic activity or cell wall biosynthesis (i.e., potential antibacterial drugs), and in the isolation/purification of MurG, including studies of its active protein/peptide fragments.

2. BACKGROUND OF THE INVENTION

2.1 Bacterial Enzymology

The emergence of resistance to existing antibiotics has rejuvenated interest in bacterial enzymology. It is hoped that detailed mechanistic and structural information about bacterial enzymes involved in critical biosynthetic pathways could lead to the development of new antibacterial agents. Because interference with peptidoglycan biosynthesis is a proven strategy for treating bacterial infections, all of the enzymes involved in peptidoglycan biosynthesis are potential targets for the development of new antibiotics. While some detailed structural and mechanistic information on some of the early enzymes in the pathway is now available, most of the downstream enzymes have proven very difficult to study.

There are two main reasons for this difficult: First, the downstream enzymes are membrane-associated, making them intrinsically hard to handle; secondly, discrete substrates for most of the downstream enzymes are either not available or not readily so. In some cases monomeric substrates are difficult to obtain in large quantities from natural sources. In other cases substrates, which may be available in large quantities from natural sources, are intractable polymeric substances. In the absence of readily available discrete substrates, it has been impossible to develop enzyme assays that can be used to measure the activity of the downstream enzymes reliably and under a well-defined set of reaction conditions. This unfulfilled need has thwarted attempts to purify many of the downstream enzymes in an active form suitable for structural characterization, much less permitted attempts to obtain detailed mechanistic information on such enzymes.

Some of the best antibiotics function by interfering with the biosynthesis of the peptidoglycan polymer that surrounds bacterial cells. With the emergence of bacterial pathogens that are resistant to common antibiotics it has become imperative to learn more about the enzymes involved in peptidoglycan biosynthesis. Although remarkable progress has been made in characterizing some of the early enzymes in the biosynthetic pathway (See, e.g., (a) Fan, C.; Moews, P. C.; Walsh, C. T.; Knox, J. R. Science 1994, 266, 439; (b) Benson, T. E.; Filman, D. J.; Walsh, C. T.; Hogle, J. M. Nat. Struct. Biol. 1995, 2, 644; (c) Jin, H. Y.; Emanuele, J. J.; Fairman, R.; Roberston, J. G.; Hail, M. E.; Ho, T.; Falk, P.; Villafranca, J. J. Biochemistry 1996, 35, 1423; (d) Skarzynski, T.; Mistry, A.; Wonacott, A.; Hutchinson, S. E.; Kelly, V. A.; Duncan, K. Structure 1996, 4, 1465; (e) Schonbrunn, E.; Sack, S.; Eschenburg, S.; Perrakis, A.; Krekel, F.; Amrhein, N.; Mandelkow, E. Structure 1996, 4, 1065. (f) Benson, T. E.; Walsh, C. T.; Hogle, J. M. Biochemistry 1997, 36, 806.), the downstream enzymes have proven exceedingly difficult to study. Part of the difficulty steams from the fact that such downstream enzymes are membrane-associated (See, e.g., (a) Gittins, J. R.; Phoenix, D. A.; Pratt, J. M. FEMS Microbiol, Rev. 1994, 13, 1; (b) Bupp, K.; van Heijenoort, J. 1993, 175, 1841.), making them intrinsically hard to handle, and partly because substrates for many of the enzymes are not readily available. (See, e.g., (a) Pless, D. D.; Neuhaus, F. C. J. Biol. Chem. 1973, 248, 1568; (b) van Heijenoort, Y.; Gomez, M.; Derrien, M.; Ayala, J.; van Heijenoort, J. J. Bacterial, 1992, 174, 3549.) These problems have impeded the development of activity assays suitable for detailed mechanistic investigations of the downstream enzymes. For a fluorescent assay to monitor MraY activity, see: Brandish, P. E.; Burnham, M. K.; Lonsdale, J. T.; Southgate, R.; Inukai, M.; Bugg, T. D. H. J. Biol. Chem. 1996, 271, 7609.

2.2. MurG

One such downstream enzyme is MurG, which is involved in peptidoglycan biosynthesis. MurG catalyzes that last intracellular step in the biosynthetic pathway of peptidoglycan biosynthesis, i.e., the transfer of UDP-N-acetylglucosamine (UDP-GlcNAc) to the lipid-linked N-acetylmuramylpentapeptide substrate, Lipid I. (See, Scheme 1, below.)

Although the murG gene is first identified in E. coli in 1980 and is sequenced independently by two groups in the early 1990's, very little is known about the MurG enzyme. There are no mammalian homologs, and no direct assays for MurG activity have been developed, in part because the lipid-linked substrate (Lipid I, Scheme 1) is extremely difficult to isolate. This lipid-linked substrate is present only in minute quantities in bacterial cells. Although it is possible to increase the quantities of lipid-linked substrate by using cells engineered to overexpress enzymes involved in the synthesis of the lipid-linked substrate, isolation remains very difficult. Moreover, the isolated substrate is hard to handle.

Consequently, MurG activity is currently assessed using crude membrane preparations by monitoring the incorporation of radiolabel from radiolabeled UDP-GlcNAc donor group into lipid-linked acceptor components in the membrane. To increase the signal, the membranes are often prepared from bacterial cultures that overexpress MraY and/or MurG. MraY is the enzyme that catalyzes the reaction that attaches the MraY substrate, UDP-N-acetyl muramic acid pentapeptide, to a lipid phosphate moiety to provide Lipid I, which is the substrate for MurG. Typically, the membrane preparations are supplemented with exogenous UDP-N-acetyl muramic acid pentapeptide for conversion to Lipid I. This MraY substrate can be readily isolated in large quantities from bacterial cultures. Although this "coupled" enzyme assay is manageable for screening of potential inhibitors of the MurG enzyme, it is not suitable for detailed mechanistic investigations, and it cannot be used to follow MurG activity during purification.

More specifically, MurG is a cytoplasmic membrane-associated enzyme which catalyzes the transfer of UDP-N- acetylglucosamine (UDP-GlcNAc) to the C4 hydrozyl of an undecaprenyl pyrophosphate N-acetylmuramyl pentapeptide substrate (Lipid I). resulting in the assembly of the disaccharide-pentapeptide building block (Lipid II, Scheme 1), which is incorporated into polymeric peptidoglycan. See, e.g., (a) Bugg, T. D. H.; Walsh, C. T. Nat. Prod. Rep. 1992, 199; (b) Mengin-Lecreulx, D.; Fluoret, B.; van Heijenoort, J. . Bacterial. 19R2, 151, 1109. As already mentioned, the muramyl pentapeptide substrate is unique to bacteria. Hence, the MurG enzyme is a potential target for the discovery or design of specific MurG inhibitors.

Despite decades of effort spent characterizing MurG activity, there is virtually no structural or mechanistic information on the enzyme. See, e.g., (a) Anderson, J. S.; Matsuhashi, M.; Haskin, M. A.; Strominger, J. L. Proc. Natl. Acad. Sci. USA 1965, 53, 881; (b) Anderson, J. S.; Matsuhashi, M.; Haskin, M. A.; Strominger, . L. J. Biol. Chem. 1967, 242, 180; (c) Taku, A.; Fan, D. P. J. Biol. Chem. 1976, 251, 6154; (d) Mengin-Lecreulx, D.; Texier, L.; van Heijenoort, J. Nucl. Acid. Res. 1990, 18, 2810; (e) Ikeda, M.; Wachi, M.; Jung, H. K.; Ishino, F.; Matsuhashi, M. Nucl. Acid Res. 1990, 18, 4014; (f) Mengin-Lecreulx, D.; Texier, L.; Rousseau, M.; van Heijenoort, J. J. Bacteriol 1991, 173, 4652; (g) Miyao, A.; Yoshimura, A.; Sato, T.; Yamamoto, T.; Theeragool, T.; Kobayashi, Y. Gene, 1992, 118, 147; (h) Ikeda, M.; Wachi, M.; Matsuhashi, M. J. Gen. Appl. Microbiol., 1992, 38, 53. Difficulties isolating Lipid I have prevented the development of a simple, direct assay for MurG activity. Consequently, it has not been possible to purify MurG in a quantifiably active form or to determine the minimal functional length; not has it been possible to carry out any detailed mechanistic studies, or to determine the substrate requirements.

Therefore, there exists a need for a direct enzyme assay that can be used both for effective screening of enzyme inhibitors and for the purification, characterization and identification of MurG its various mutants and active fragments thereof.

Scheme 1.
The reaction catalyzed by MurG in the context of peptidoglycan biosynthesis.
The composition of the pentapeptide varies with micro-organism, particularly at the third position (shown here as L-Lys).

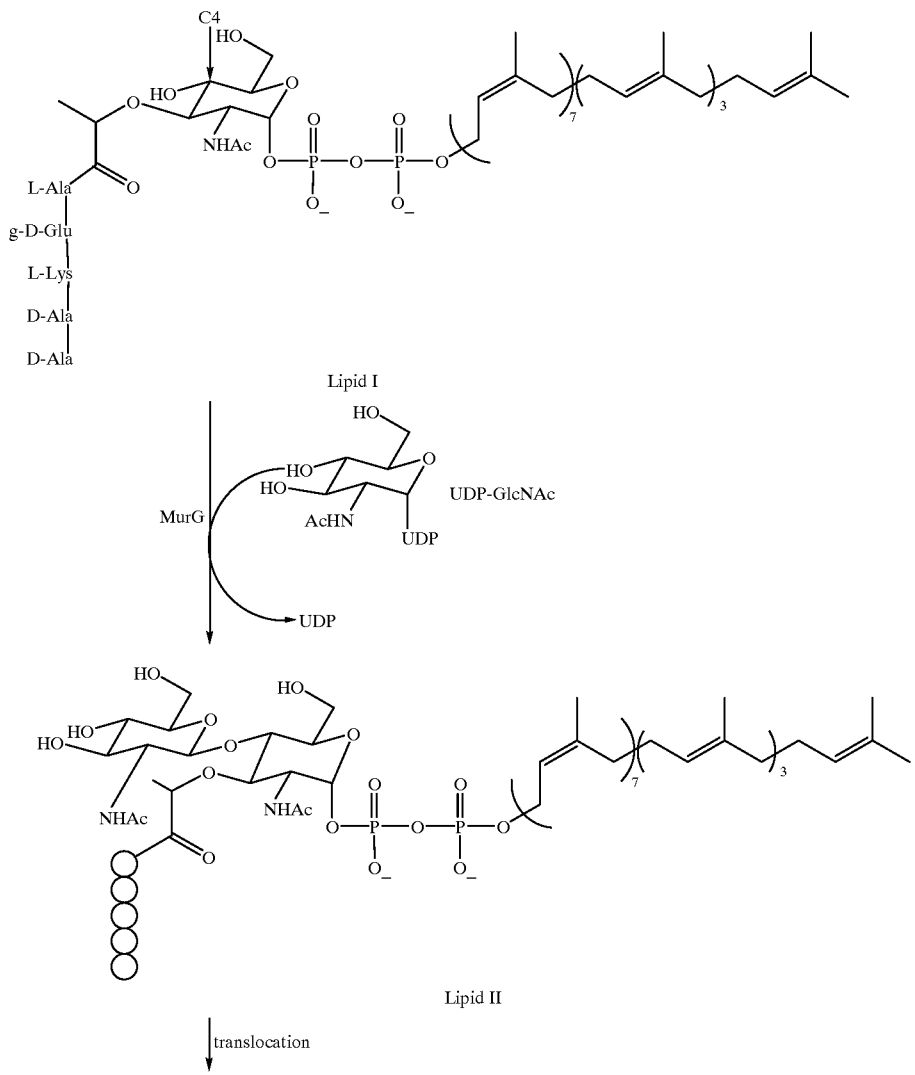

-continued

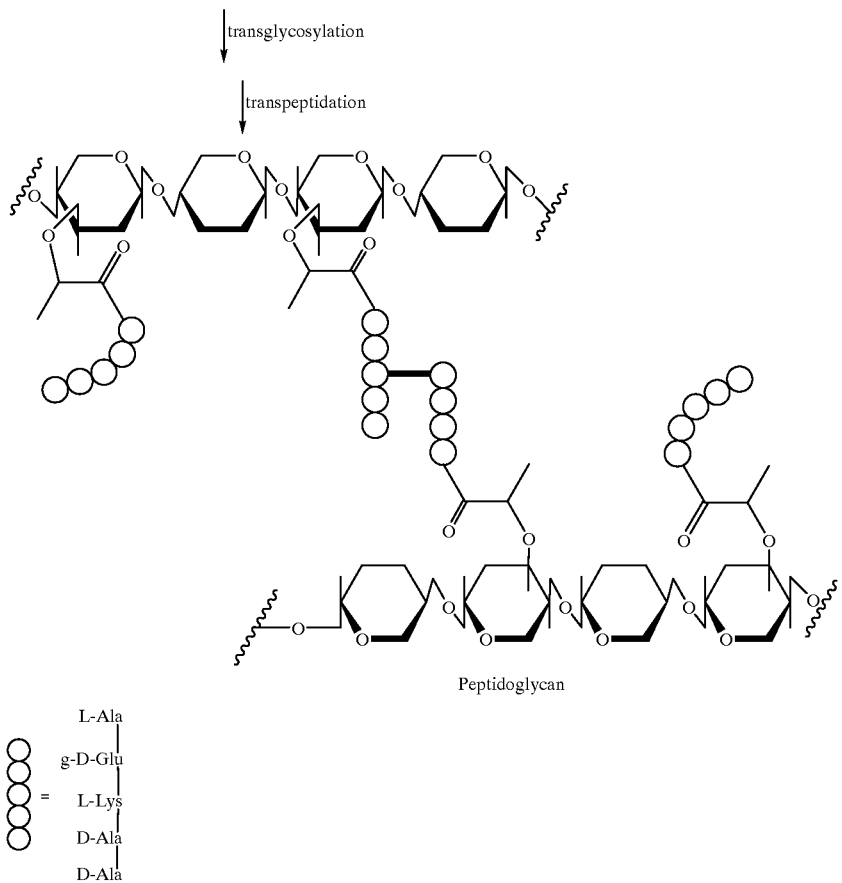

Peptidoglycan

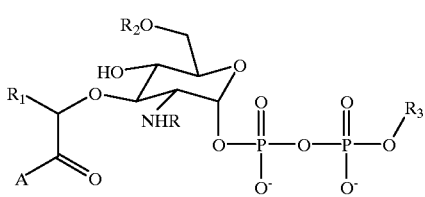

3. SUMMARY OF THE INVENTION

Substrate analogs for MurG enzyme, a GlcNAc transferase, are disclosed. For the first time, a substrate analog of Lipid I, as shown above in Scheme I, (i) having a structure that is accepted by at least wild type MurG enzyme such that a labeled coupling product is produced by the GlcNAc transferase activity of the enzyme in the presence of the substrate analog and labeled UDP-GlcNAc, and (ii) having structural features that facilitate the separation of labeled UDP-GlcNAc from the labeled coupling product.

In particular, a substance is described herein, which comprises the chemical moiety of the formula:

(I)

in which "R" is an acyl group comprising 2 or more carbon atoms, "$R_1$" is a substituted or unsubstituted alkyl group comprising 1 or more carbon atoms, "$R_2$" is a hydrogen or a substituted or unsubstituted alkyl group comprising 1 or more carbon atoms, "A" is a substituted or unsubstituted amino acid residue or a peptide comprising 2 or more substituted or unsubstituted amino acid residues, "$R_3$" is a substituted or unsubstituted alkyl group comprising 5 or more carbon atoms, the substance exhibiting a binding affinity for at least wild type MurG enzyme and provided that the substance is not Lipid I, the natural substrate of wild type MurG enzyme. More particularly, the substance of the invention serves as an acceptor for the GlcNAc transferase activity of at least wild type MurG enzyme or its homologs.

Also disclosed is a method of detecting GlCNAc transferase activity in a sample suspected of containing a protein or an active fragment thereof exhibiting GlcNAc transferase activity. Preferably the method comprises (a) providing a sample suspected of containing a protein or an active fragment thereof exhibiting GlcNAc transferase activity; (b) contacting the sample with effective amounts of labeled GlcNAc substrate and a substance comprising the chemical moiety of the formula (I), above, under conditions effective to provide a labeled coupling product comprising labeled GlcNAc coupled to the substance via a glycosidic bond in the presence of a protein or an active fragment thereof exhibiting GlCNAc transferase activity; and (c) detecting the formation or presence of the labeled coupling product, which is indicative of GlcNAc transferase activity in the sample.

It is also an objective of the present invention to provide an assay for detecting GlcNAc transferase activity in a sample suspected of containing a protein or an active fragment thereof exhibiting GlCNAc transferase activity comprising a compound of the formula (I), above. A screen and methods of utilizing same are also contemplated by the present invention. In particular, a screen is provided for compounds exhibiting potential antibacterial activity comprising (i) a protein or an active fragment thereof exhibiting GlcNAc transferase activity, (ii) a substance comprising the chemical moiety of the formula (I), above, and (iii) a labeled GlcNAc substrate.

Additionally, the method of this invention provides a detection step comprising binding the "A" or "$R_3$" groups of formula I to a solid support via a biotin tag, wherein said solid support includes an avidin or streptavidin coated resin. This step provides a continuous monitoring of product formation via the use of scintillation proximity assay. Furthermore, the separation of biotin-labeled substance involves filtration through an avidin-coated resin.

In a preferred embodiment of the invention "$R_3$" may be selected from H, an aliphatic group comprising 1 to about 50 carbon atoms, an aromatic or heteroaromatic group comprising 3 to about 55 carbon atoms, pyrophosphate protecting groups and pharmaceutically acceptable salts thereof.

Additionally, a method detection step comprises binding said "A" or "$R_3$" to a solid support via a biotin tag, wherein said solid support includes an avidin or streptavidin coated resin.

Hence, substrate analogs are prepared, which are used in an enzyme assay for MurG or MurG-like activity. A direct assay for MurG activity is thus provided.

These and other objects of the invention are described further, below, along with the preferred embodiments of the invention.

4. BRIEF DESCRIPTION OF THE FIGURE

FIG. 1. Plot of GlcNAc transfer as a function of the concentration of substrate analog 5b and concentration of active MurG enzyme. All reactions are run in 100 mM Tris-HCl, pH 7.6, 1 mM $MgCl_2$, with 0.5–1.0 µg total protein and 9.4 µM 14C-UDP-GlcNAc (265 mCi/mmol). Reactions for curves A, B, C, and D are carried out using a cell lysate from a transformed BI.21(DE2)pLysS strain that overexpresses MurG: A)-■7.1 µM, 5b; B)-♦ 3.5 µM 5b; C)-● 0.71 µM 5; D)-○ 7.1 µM 5b+heat treated cell lysate (65° C., 5 min.). Reactions for curve E are carried out using a BL21(DE3)pLysS cell lysate expressing only endogenous levels of MurG: E)-V 7.1 µM 5b.

Figure 2A:
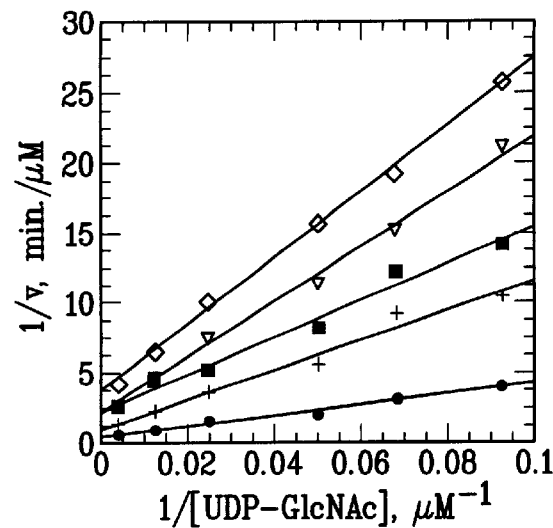

FIG. 2(a). Double reciprocal plots of the initial rate data with UDP-GlcNAc as the varied substrate. Initial rates are measured at fixed acceptor 1b concentrations of 7 µM (◊), 10 µM (V), 15 µM, (■), 30 µM (+), 100 µM (●). 0.08 µM of purified MurG is used for each reaction.

Figure 2B:
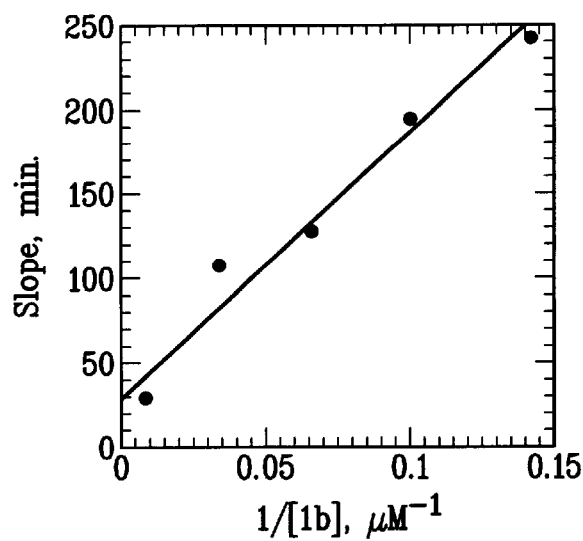

FIG. 2(b). Secondary plots of the slope.

Figure 2C:
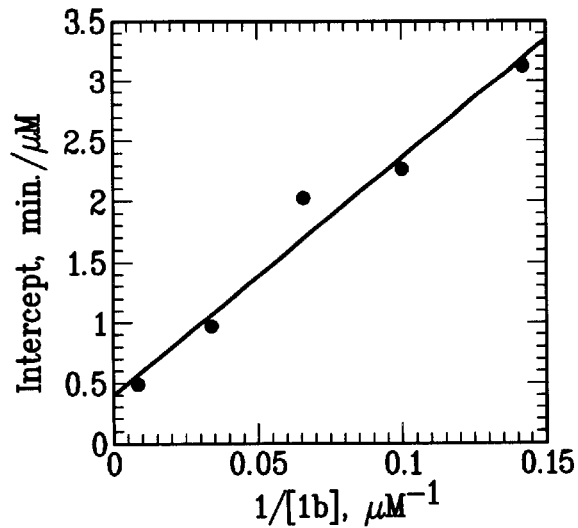

FIG. 2(c). Intercept versus $[1b]^{-1}$. Analysis of the data assuming a rapid equilibrium sequential mechanism yields the following kinetic parameters: $K_{UDF-GLCNAL}$=110±30 µM, $K_{1b}$=60±15 µM.

Figure 3A:
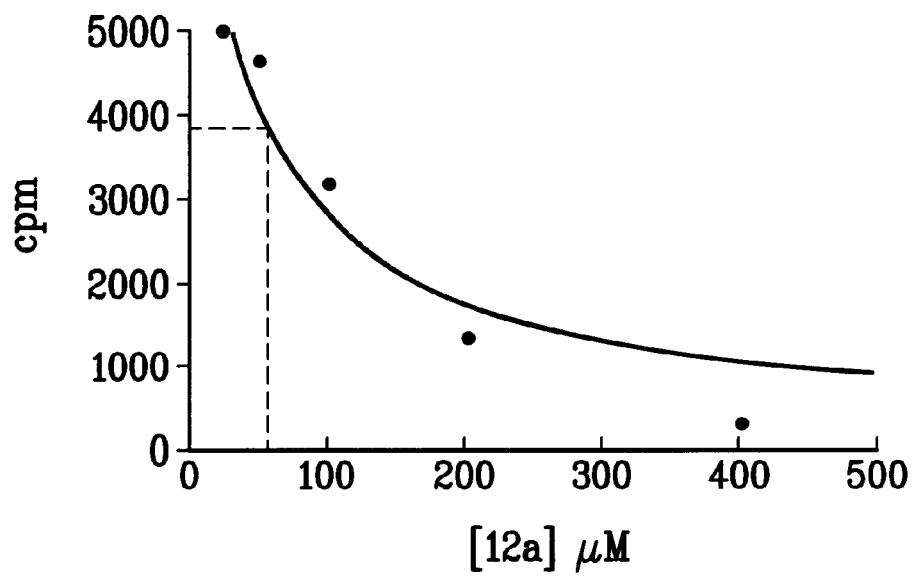
Figure 3B:
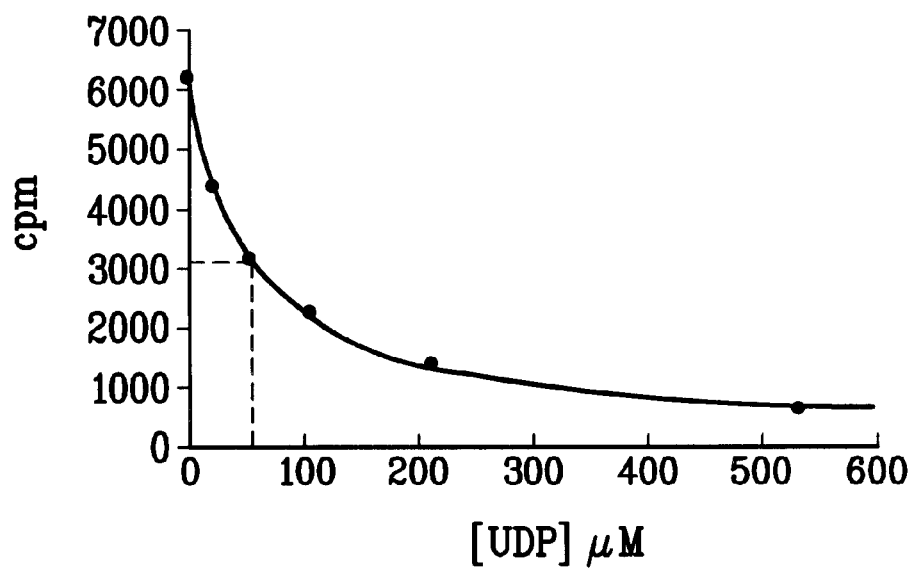

FIG. 3. IC50 measurements for compound 12a and UDP. All the assays are performed under the same conditions with 18 µM 1b and 34.3 µM UDP-GlCNAc. Each $ID_{50}$ value is determined by fitting five or six data points to equation:

$$\frac{v_1}{v_0} = \frac{l}{1 + \frac{(l)}{IC_{50}}}$$

where $v_I$ is the initial rate in the presence of inhibitor at concentration (1), and $v_o$ is the initial rate without inhibitor.

Figure 4:
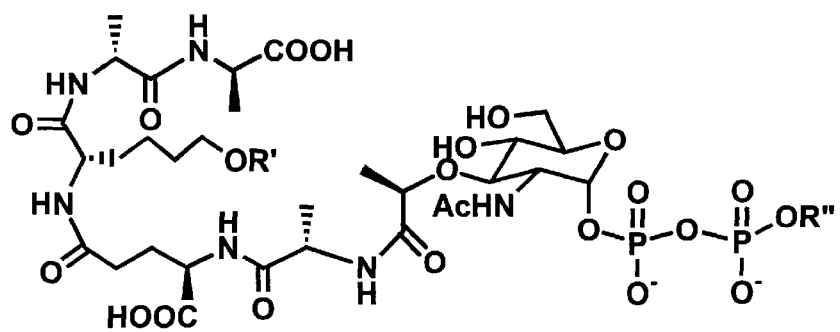
Figure 4:
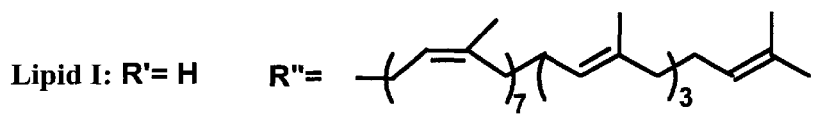
Figure 4:
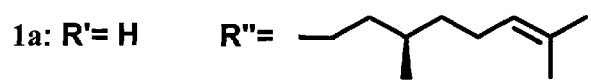
Figure 4:
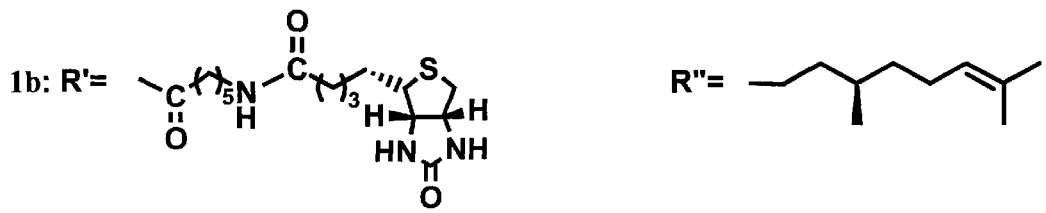

FIG. 4. Structure of Lipid I and analogs (1a, 1b).

Figure 5:
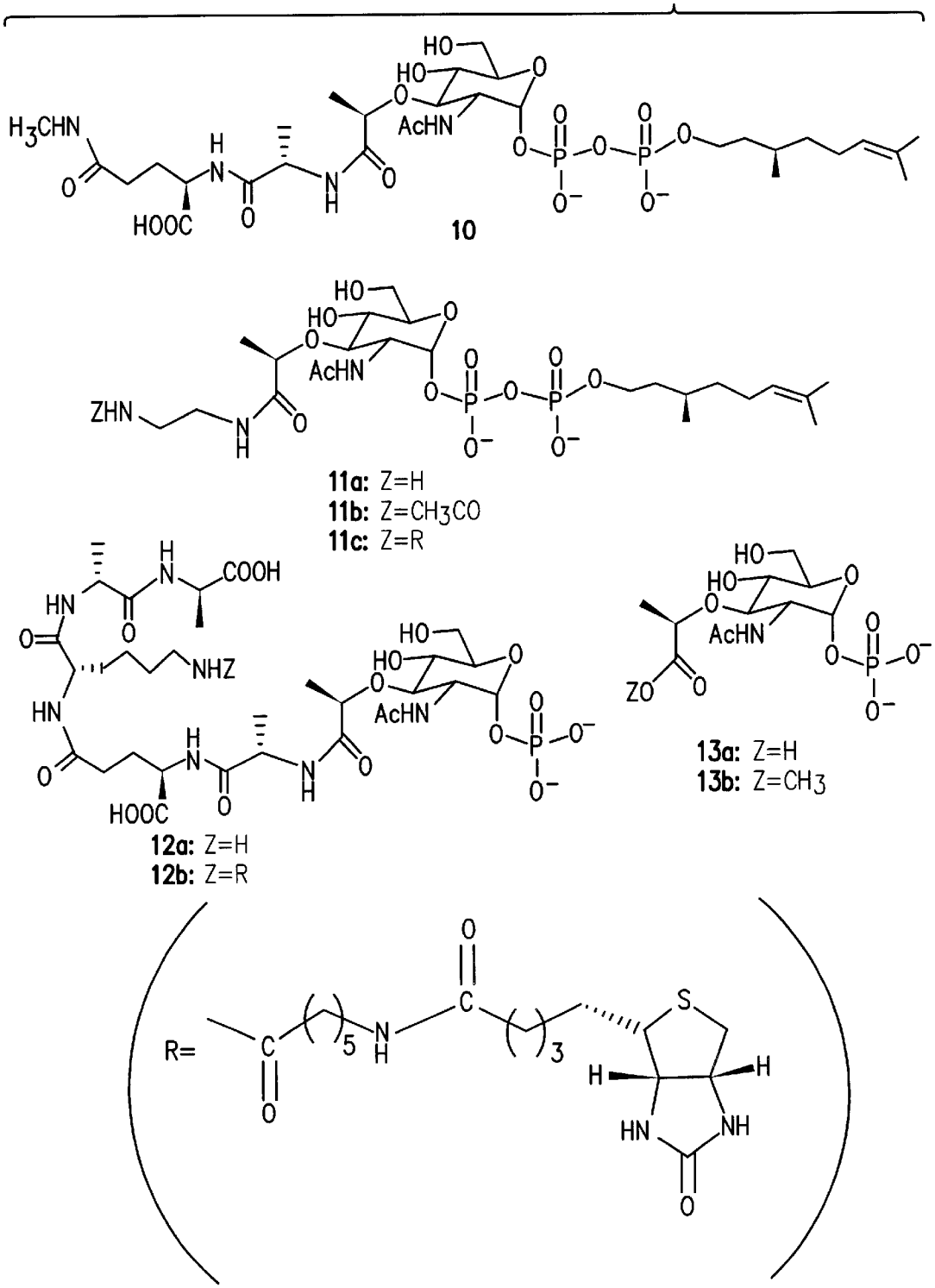

FIG. 5. Substrate-based inhibitors of MurG activity.

Figure 6:
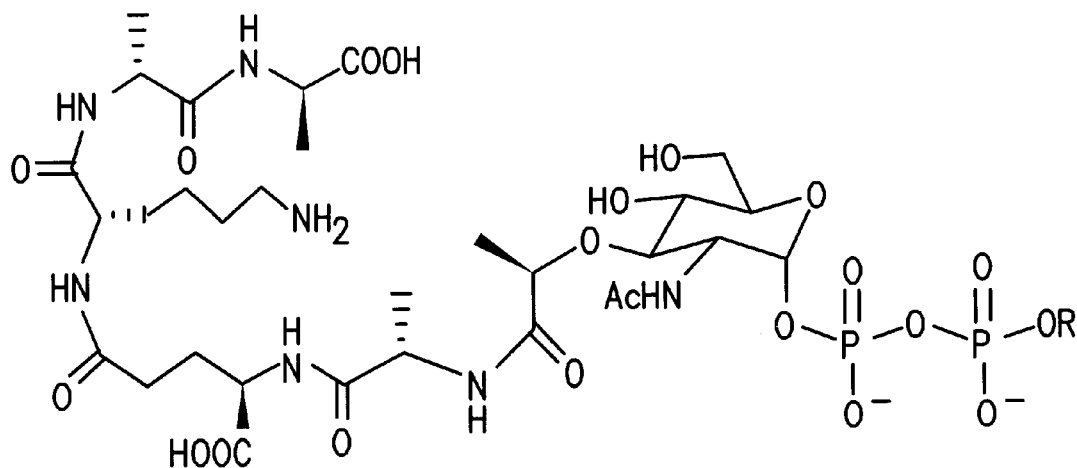

FIG. 6. Alternative acceptors for MurG.

Figure 7:
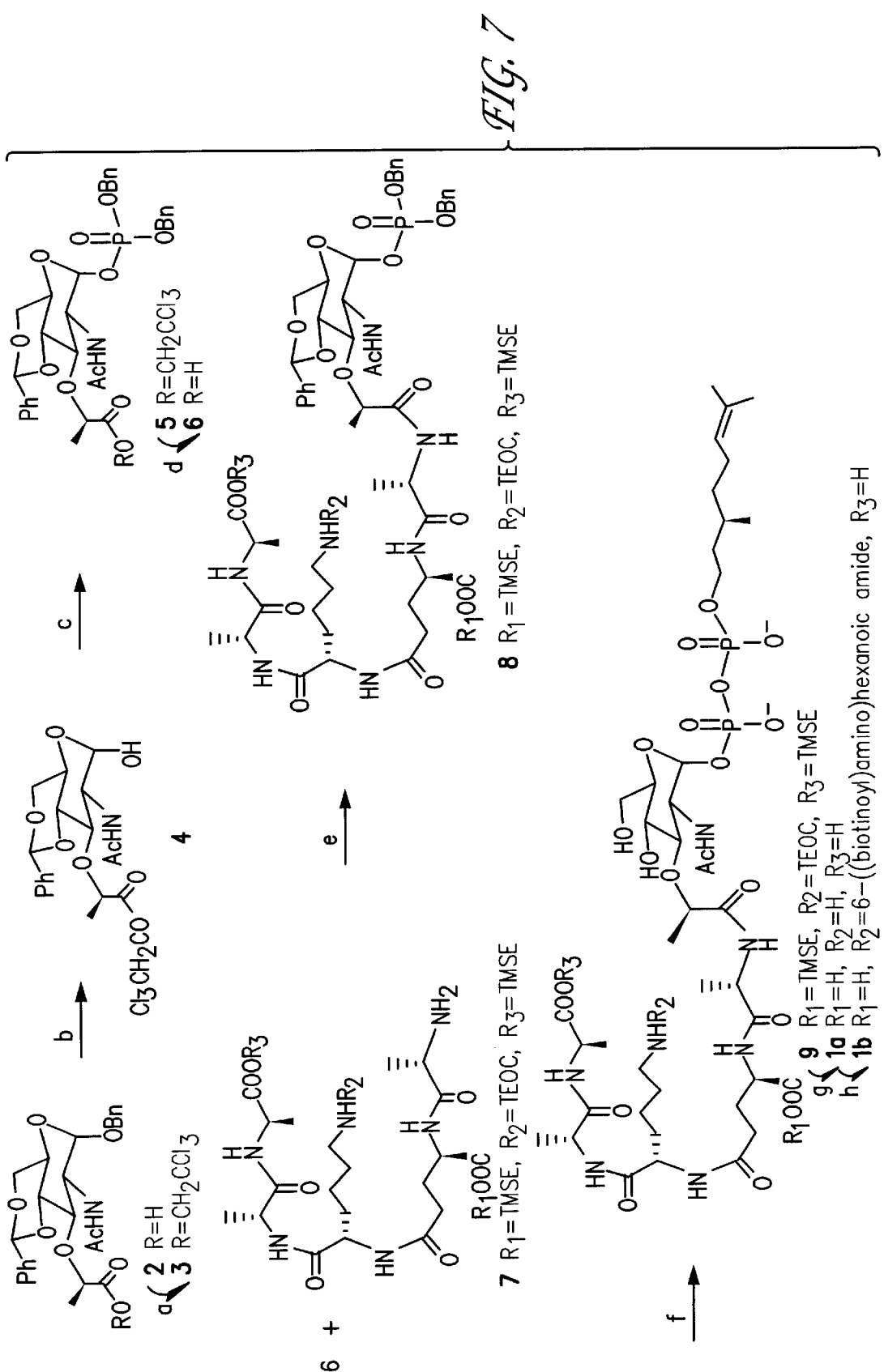

FIG. 7, Synthesis of lipid I analogs (1a, 1b). Reagents and conditions: (a) $CCl_3CH_2OH$, DCC/DMAP, THF, rt, 4 h, 80%; (b) 1. $H_2$/Pd, EtOAc, rt, 0.5 h; 2, $PhCH(OCH_3)_2$, cat TsOH, DMF, rt, 10 h, 81%, 2 steps; (c) $iPr_2NP(OBn)_2$, $^1$H-tetrazole, $CH_2Cl_2$, –20° C.–>0° C., 0.5 h, then mCPBA, –40° C., 0.5 h, then mCPBA, –40° C.–>25° C., 2 h, 70%; (d) Zn dust, 90%, $AcOH/H_2O$, rt, 1 h, 91%; (e) HOBt, PyBop, DIEA, DMF, 0° C., 30 min, 87%; (f) 1. $H_2$/Pd, $CH_3OH$, rt, 30 min, then py; 2. (R)-(+)-β-Citronellol-$OPO_3PO(OPh)_2$, py, $CH_2Cl_2$, rt, 18 h, 68%; (g) TBAF, DMF, rt, 24 h, 93%; (h) 6-((biotinoyl)amino)hexanoic acid succinimide ester, $NaHCO_3$, $H_2O$/dioxane, rt, 2 h, 80%.

Figure 8:
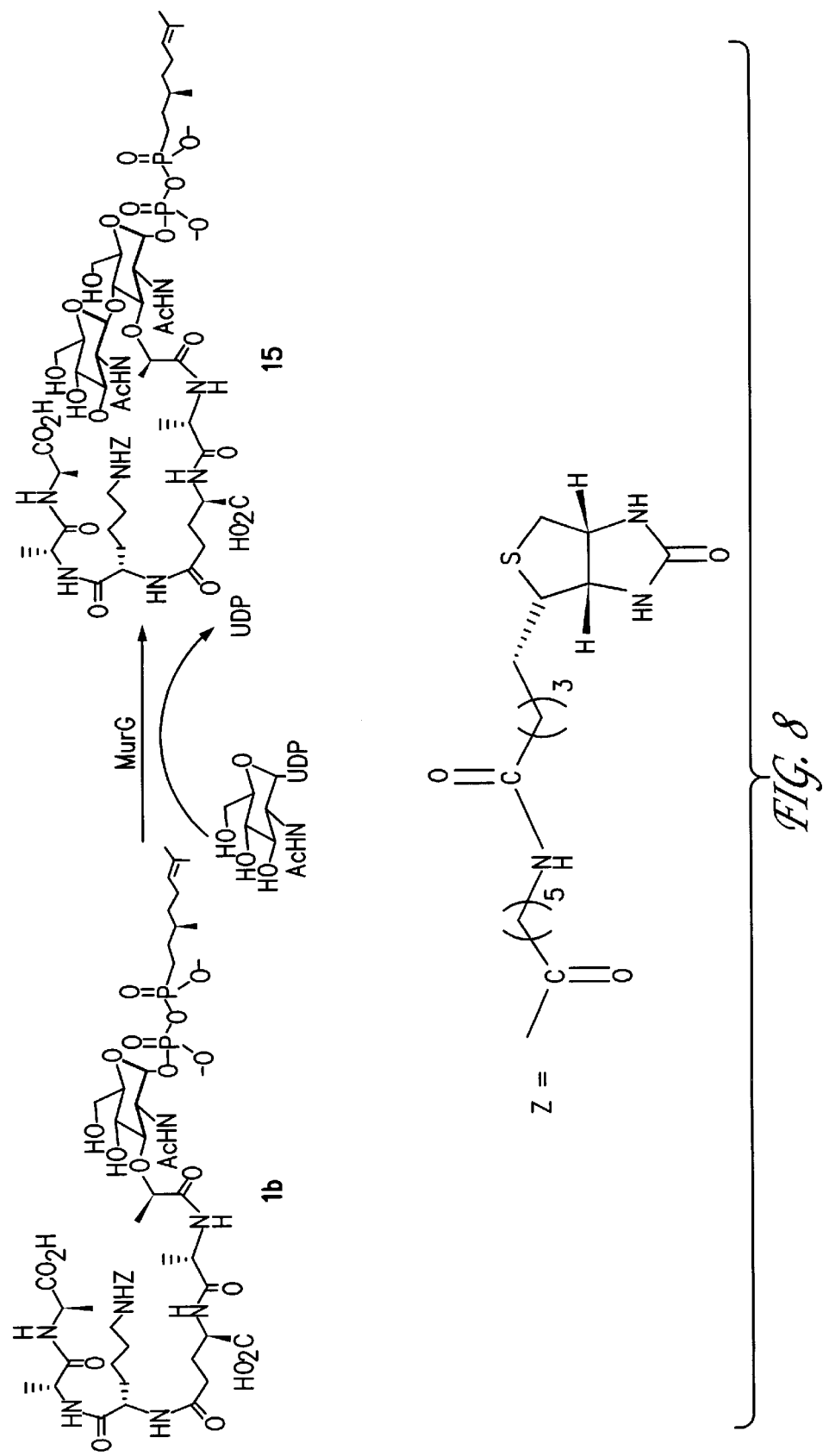

FIG. 8. Synthesis of disaccharide by MurG.

5. DETAILED DESCRIPTION OF THE PREFERRED EMBODIMENTS

5.1. General Aspects of the Invention

The present invention contemplates a substance comprising the chemical moiety of the formula:

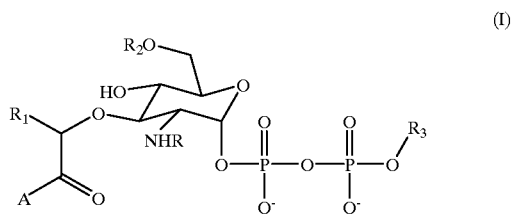

(I)

in which "R" is an acyl group comprising 2 or more carbon atoms, "$R_1$" is a substituted or unsubstituted alkyl group comprising 1 or more carbon atoms, "$R_2$" is a hydrogen or a substituted or unsubstituted alkyl group comprising 1 or more carbon atoms, "A" is a substituted or unsubstituted amino acid residue or a peptide comprising 2 or more substituted or unsubstituted amino acid residues and "$R_3$" is a substituted or unsubstituted alkyl group comprising 5 or more carbon atoms, such as 15 to 40 carbon atoms (see 5.3) or 10 to 40 carbon atoms based on citronellol containing 10 carbon atoms. Preferably, the substance of the invention (sometimes referred to herein as a substrate analog or, simply, compound) exhibits a binding affinity for at least wild type MurG enzyme. More preferably, the substance of the invention serves as an acceptor for the GlcNAc transferase activity of at least wild type MurG enzyme. It is important to note that the substance of the invention is not so broadly defined as to encompass Lipid I, the natural substrate of wild type MurG enzyme.

It should be evident to one of ordinary skill that the substance disclosed and described herein can also possess inhibitor activity against the GlcNAc transferase activity of at least wild type MurG enzyme, its homologs and, possibly, certain mutant forms thereof, depending in part on the strength of its binding affinity with the protein or its active fragments. That is, a substrate analog of the present invention, by binding tenaciously to the protein or active fragment thereof, can potentially inhibit the ability of MurG or a MurG-like enzyme to catalyze the glycosylation reaction that results in the transfer of GlcNAc to the C4 hydroxyl position of the N-acetylmuramic acid moiety of Lipid I. Of course, MurG and its homologs are derived from *E. coli* and other gram-negative bacteria. Gram-positive bacteria, such as *B. subtillis, E. faecalis, E. hirae,* as well as *M. tuberculoris,* are also known to harbor homologs of MurG. In one embodiment of the present invention, a pharmaceutical composition is provided that comprises a pharmaceutically acceptable salt of a substance of the present invention and a pharmaceutically acceptable carrier.

Accordingly, in a preferred embodiment of the invention, "R" is an acyl group including, but not limited to, acetyl, proprionyl, butanoyl, pentanoyl, hexanoyl and the like. The group "$R_1$" is a substituted or unsubstituted alkyl group including, but not limited to, methyl, ethyl, propyl, butyl, pentyl, hexyl, phenyl, benzyl, tolueyl, anthracyl and the like. The group "$R_2$" is a hydrogen or a substituted or unsubstituted alkyl group including, but not limited to , methyl, ethyl, propyl, butyl, pentyl, hexyl, phenyl, benzyl, tolueyl, anthracyl and the like.

Hence, the term "alkyl" group can encompass an aliphatic or an aromatic group, and the term "substituted" means that the particular alkyl group can have substituents including, but not limited to, additional alkyl groups, heteroatoms or functional groups containing heteroatoms, including, but not limited to, alcohols, ethers, carboxylic acids, esters, amides, amines, alkylamines, thiols, sulfides, sulfates, sulfoxides, sulfonic acids, phosphoric acids, phosphate esters, phosphides, phosphonates, phosphoramidates and the like. Any acyl group can have 2 or more carbon atoms, and any alkyl group can have 1 or more carbon atoms. Each group can have as many as 25 carbon atoms, preferably up to 20 carbon atoms, more preferably up to 15, most preferably up to 10 carbon atoms.

In one embodiment of the invention, the group "$R_3$" may be a substituted or unsubstituted alkyl group including, but not limited to, methyl, ethyl, propyl, butyl, pentyl, hexyl, phenyl, benzyl, tolueyl, naphthyl, anthracyl and the like. More particularly, the group "$R_3$" comprises a mimic of the 55-carbon hydrocarbon anchor found in the natural MurG substrate, Lipid I. Such mimics include, but are not limited to, citronellol, other polyprenol derivative, or an aromatic group. In addition, the group "$R_3$" can be bound to a solid support, such as a synthetic resin or bead.

The group "A" is broadly contemplated to encompass any substituted or unsubstituted amino acid residue or any peptide comprising 2 or more substituted or unsubstituted amino acid residues. The group "A" can have as few as one, tow, or three amino acid residues, or many as 10 or more amino acid residues, preferably no more than ten, more preferably no more than eight, most preferably no more than five (e.g., a pentapeptide). Other chemical moieties may be associated with the group "A," preferably covalently attached, including but not limited to linker groups, labeling groups (such as radiolabeled groups, fluorescent groups and the like), affinity groups (such as biotin, avidin, streptavidin and the like or haptens, such as dinitrophenol, dipoxegenin and the like), hydrophobic groups, hydrophilic groups, and the like. In one embodiment of the invention biotin is conjugated to the group "A", in which the biotin moiety is attached covalently (e.g., to an amino group of an amino acid residue) either directly or via a linker moiety.

In a preferred embodiment, the amino acid residue attached to the lactic acid moiety of the substance of the formula (I) is Ala. A D-γ-linked glutamic acid residue is preferably attached next to this first alanine residue. A lysine residue (L-Lys) is preferably attached next to this glutamic acid residue, particularly for gram-positive bacteria. For gram-negative bacteria, this third residue is preferably meso-diaminopimelate or "m-DAP". Other residues at this position include, but are not limited to, L-alanine, L-homoserine, L-diaminobutyric acid, L-glutamic acid, L-ornithine, LL-DAP, as well as the meso-form, referred to, above. Still others may include L-Orn, LL-DPm, m-HyDpm, L-Dab, L-HyLys, N$^γ$-Acetyl-L-Dab, L-Hsr, L-Ala, or L-Glu. A preferred amino acid sequence for a pentapeptide is L-Ala-D-γ-Gu-L-Lys-D-Ala-D-Ala, the amino terminal end of which is attached to the lactic acid moiety of the substance of the formula (I) via an amide bond. Yet another suitable amino acid sequence may be L-Ala-D-γ-Glue-meso-DAP-D-Ala-D-Ala. A tripeptide sequence of potential advantage is L-Ala-D-γ-Glu-L-Lys, optionally substituted at the L-Lys amino acid residue with an affinity "handle," such as biotin, avidin, streptavidin, an immunoglobulin, Protein A, and the like or fragments thereof, or haptens, such as dinitrophenol, digoxegenin and the like. Still possible is a dipeptide arrangement, including but not limited to L-Ala-D-Lys, once again optionally substituted at the D-Lys amino acid residue.

In a method of the present invention GlcNAc transferase activity is detected in a sample suspected of containing a protein or an active fragment thereof exhibiting GlcNAc transferase activity. The method includes the steps of: (a) providing a sample suspected of containing a protein or an active fragment thereof exhibiting GlcNAc transferase activity, (b) contacting the sample with effective amounts of labeled UDP-GlcNAc substrate and a substance comprising the chemical moiety of the formula (I), above, provided that the substance is not Lipid I, the natural substrate of wild type MurG enzyme, under conditions effective to provide a labeled coupling product comprising labeled GlcNAc coupled to the substance via a glycoside bond in the presence of a protein or an active fragment thereof exhibiting GlcNAc transferase activity; and (c) detecting the formation or presence of the labeled coupling product, which is indicative of GlcNAc transferase activity in the sample. Preferably, the labeled GlcNAc substrate is labeled UDP-GlcNAc.

In the inventive method at least a portion of the sample may comprise a portion of a lysed bacterial culture, a portion of a supernatant thereof, a portion of a membrane fraction thereof, a portion of a protein fraction thereof, a purified enzyme, purified or synthesized lipid or mixtures of same.

Detection of the formation or presence of the labeled coupling product can be effected in a number of ways, apparent to those of ordinary skill. For example, the detection step may comprise separation of the labeled coupling product from labeled UDP-GlcNAc substrate. As discussed elsewhere in this disclosure, separation of the labeled species can be accomplished using a variety of approaches, including but not limited to, hydrophobic capture, affinity chromatography, or other solid phase separation techniques. Quantification of the labeled coupling product can then follow depending on the nature of the label utilized.

Consistent with the objectives of the present invention an assay is provided for detecting GlcNAc transferase activity in a sample suspected of containing a protein or an active fragment thereof exhibiting GlcNAc transferase activity. An assay of the invention comprises a compound of the formula:

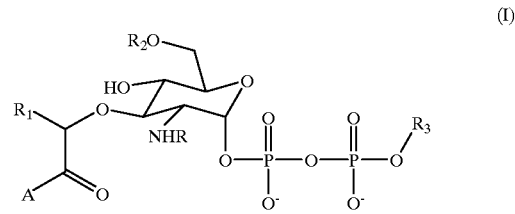

(I)

in which "R" is an acyl group comprising 2 or more carbon atoms, "$R_1$" is a substituted or unsubstituted alkyl group comprising 1 or more carbon atoms, "$R_2$" is a hydrogen or a substituted or unsubstituted alkyl group comprising 1 or more carbon atoms, "A" is a substituted or unsubstituted amino acid residue or a peptide comprising 2 or more substituted or unsubstituted amino acid residues, "$R_3$" is a substituted or unsubstituted alkyl group comprising 5 or more carbon atoms, the substance able to form a coupling product with a GlcNAc substrate in the presence of a protein or an active fragment thereof exhibiting GlcNAc transferase activity, provided that the substance is not Lipid I, the natural substrate of wild type MurG enzyme. The assay further comprises a labeled GlcNAc substrate.

A screen for compounds exhibiting potential antibacterial activity is also contemplated. Such a screen comprises: (i) a protein or an active fragment thereof exhibiting GlcNAc transferase activity, (ii) a substance comprising the chemical moiety of the formula (I), above, the substance able to form a coupling product with a GlcNAc substrate in the presence of a protein or an active fragment thereof exhibiting GlcNAc transferase activity, provided that the substance is not Lipid I, the natural substrate of wild type MurG enzyme, and (iii) a labeled GlcNAc substrate.

Thus, a screen including the enzyme MurG, or an active fragment thereof, is brought into contact with a substrate analog, such as a substance of the formula (I), in the presence of labeled GlcNAc substrate. The enzyme, of course, would catalyze the coupling of the labeled GlcNAc (e.g., from C-14 labeled UDP-GlcNAc) to the C4-hydroxyl group of the muramic acid moiety of the substrate analog. The formation of labeled coupling product is then monitored over time to product a graph, such as that presented in FIG. 1. (The coupling product may first have to be separated from labeled GlcNAc substrate, e.g., by column chromatography, HPLC, filtration (if the reaction is conducted in the solid phase) and the like.) A potential inhibitory compound (or compounds) is then added to the mixture, such as the control mixture described above, and the decrease in the production of labeled coupling product is monitored, preferably as a function of the concentration of the potential inhibitory compound.

5.2. The Preparation Of a Substrate Analog

Our first synthetic target, 8 (above, and Scheme 2, below), differs from Lipid I in that the 55 carbon undecaprenol chain has been replaced by the ten carbon chain of citronellol. A shorter lipid chain is chosen because long chain lipids are difficult to handle; a lipid containing saturated isoprenol unit is further chosen because allylic pyrophosphates are unstable. Although MurG is a membrane associated enzyme, which recognizes a lipid-linked substrate, the chemistry takes place on the C4 hydroxyl of the lipid-linked substrate, which is far removed from the lipid anchor. Therefore, it is hoped that alteration of the lipid can be accomplished without destroying substrate recognition.

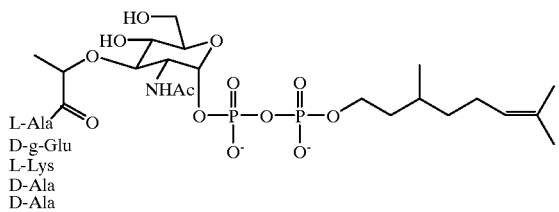

To make 8 (See, Scheme 2, below), muramic acid derivative 1 (available from Sigma) is converted to the anomeric dibenzyl phosphate 5 in 5 steps and coupled to the protected pentapeptide 13. Chen, J.; Dorman, G.; Prestwich, G. J. Org. Chem. 1996, 61, 393. The silyl protecting groups on the Lys and Glu are preferred for facile deprotection under mild conditions. Hence, the C-terminus of the peptide can be a methyl ester, as shown, or a trimethylsilyl ethyl ester.

The protected pentapeptide is synthesized on a D-Ala-FMOC Sasrin resin (available from Bachem Biosciences) in 11 steps in an overall yield of 15% (See, Method 4, below). Experimental details are provided in the Examples Section, below. Hydrogenolytic deprotection produces the anomeric phosphate, which is treated with diphenyl citronellol pyrophosphate to produce 7 (See, Scheme 2). Diphenyl citronellol pyrophosphate (10, Method 1, below) is generated in situ by treating citronellol phosphate with diphenyl chlorophosphate (See, Example Section, below; see, also: Warren, C. D.; Jeanloz, R. W. Meth. Enzymol. 1978, 50, 122.) For other methods to form glycosyl pyrophosphates, see; (a) Imperiali, B.; Zimmerman, J. W. Tet. Lett. 1990, 45, 6485; (b) Wittmann, V.; Wong, C.-H. J. Org. Chem. 1997, 62, 2144. The pyrophosphate exchange reaction takes place readily in the presence of the unprotected sugar hydroxyls. Finally, the side chain protecting groups on the peptide are removed with TBAF, which also hydrolyzes the C-terminal methyl ester to give the desired product 8. It should be noted that 8 is both acid- and base-sensitive. The synthesis minimizes exposure to acid and base, while providing for a convergent approach that allows independent modification of all three building blocks, the peptide, the carbohydrate, and the lipid.

Thus, using the same general scheme described above and further illustrated below (in which TMSE is trimethylsilylethyl, TEOC is trimethylsilylethyloxycarbonyl and N-linker is 6-aminohexanoic acid), one can prepare a variety of compounds to define the requirements for substrate binding.

Scheme 2.
Synthesis of the lipid analogue

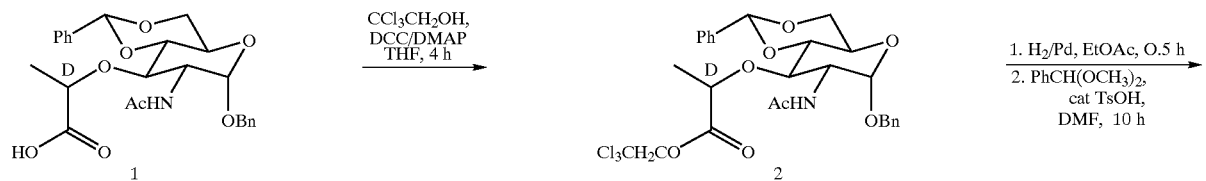

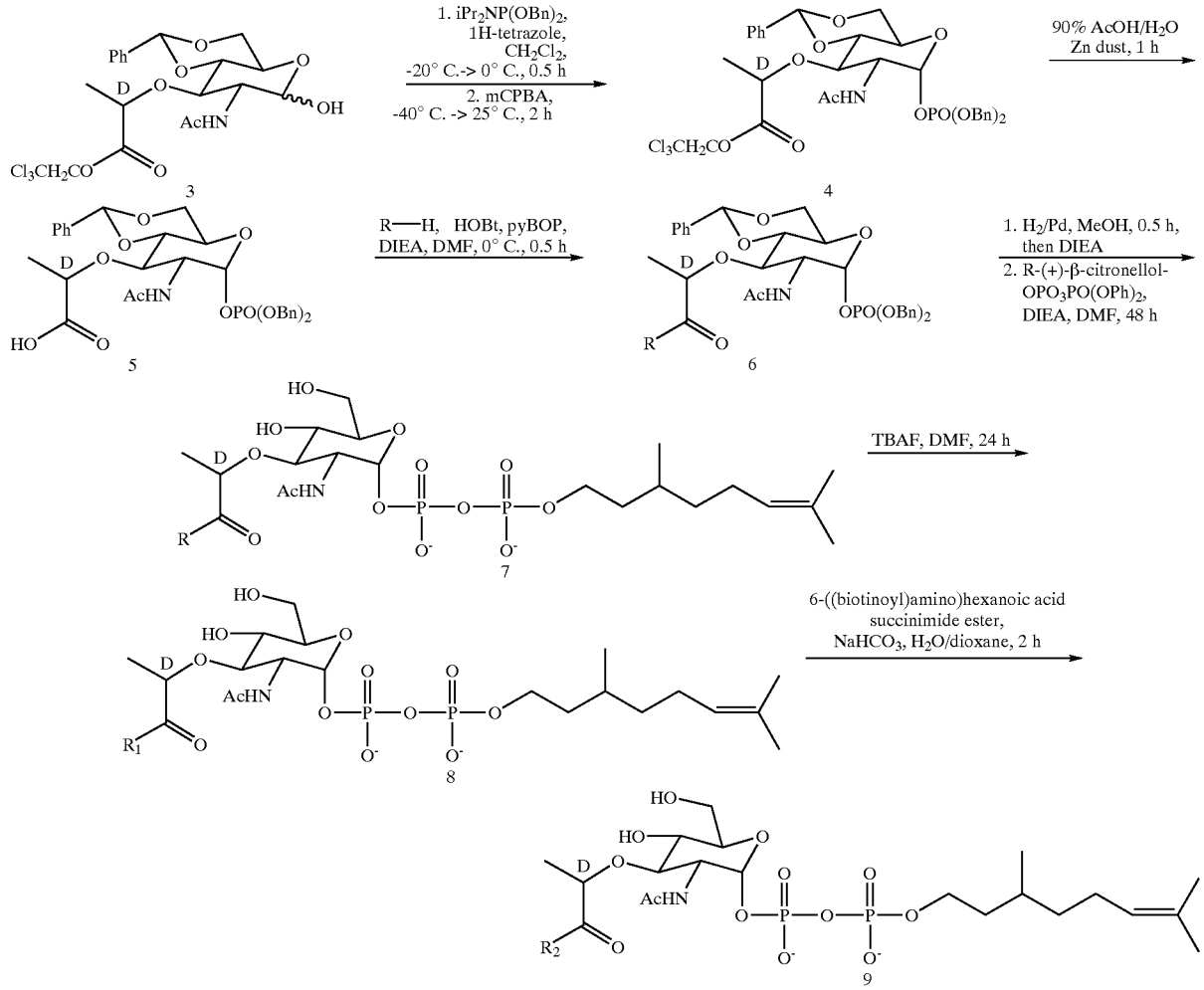

R = —NH-L-Ala-γ-D-Glu(O-TMSE)-L-Lys(N-TEOC)-D-Ala-D-Ala-OCH₃
R₁ = —NH-L-Ala-γ-D-Glu-L-Lys-D-Ala-D-Ala-OH
R₂ = —NH-L-Ala-γ-D-Glu-L-Lys(N-linker-Biotin)-D-Ala-D-Ala-OH

5.3. GlcNAc Transferase Assay

Initial attempts to use substrate 8 in MurG activity assay reveals some difficulties in separating radiolabeled product from excess labeled UDP-GlcNAc, using relatively crude separation methods like paper chromatography or thin layer chromatography. Hence, in certain applications, it may be preferable to adjust the length of the lipid chain to facilitate removal of excess labeled UDP-GlcNAc. For instance, a longer lipid chain (e.g., ca. $C_{15}$–$C_{40}$) may facilitate a separation method using a hydrophobic resin or suitable filter to take advantage of non-specific lipid-lipid interactions. What is more, a tether to a solid phase resin may be more preferable in a commercial embodiment of the invention. Still another alternative comprises an affinity group, such as biotin, an IgG binding domain, or a hapten, such as dinitrophenol, digoxegenin and the like, which is attached to the substrate analog to facilitate separation by affinity chromatography suing an affinity resin comprising avidin/streptavidin or Protein A, respectively.

The evidence suggests that MurG is relatively insensitive to the identity of the third amino acid residue in the peptide chain. E. coli strains (e.g., Bl21) make a muramyl pentapeptide substrate with meso-diaminopimelic acid (m-DAP) rather than L-lysine. E. coli MurG accepts these lysine analogs. Fluoroescently labeled analogs are also accepted by some strains: Weppner, W. A.; Neuhaus, F. C. J. Biol. Chem. 1978, 253, 472; White, D. Physiology and Biochemistry of Prokaryotes Oxford Univ. Press:New York, 1995, pp 212–223. Accordingly, the third amino acid residue makes a convenient location for attaching substituents onto the amino acid/peptide moiety. In a preferred embodiment of the invention, an affinity label substituted L-Lys is used as the third amino acid residue of the peptide chain. More preferably a biotin moiety is linked to the free amino group of lysine via a tether comprising a bifunctional aliphatic agent, such as 6-aminohexanoic acid, although shorter or longer tethers can be used. Tethers of various lengths, which are attached to certain molecules of interest, such as biotin, chromophores, fluorophores and the like, are commercially available.

In this manner, biotin is attached (Scheme 2) (6-{(biotinoyl)amino}hexanoic acid succinimide ester can be purchased from Molecular Probes, Inc.) to the ε amino group of the lysine residue via the carboxylic acid group of the 6-aminohexanoic acid linker so that radiolabeled product can be readily separated from other radioactive components in the reaction mixture using an avidin-derivatized resin (Tetralink™ Tetrameric Avidin Resin, Promega). The ability of MurG to recognize the biotin-labeled substrate 9 is evaluated by counting the radioactivity that binds in the resin after incubation of various crude membrane preparations with 9 and $^{14}$C-UDP-GlcNAc. (See, e.g., Baker, C. A. Poorman, R. A.; Kezdy, F. J.; Staples, D. J.; Smith C. W.; Elhammer, A. P. Anal. Biochem. 1996, 239, 20.) The reaction is rapid and efficient with a bacterial culture that overexpresses MurG but barely detectable with a culture expressing only endogenous levels of MurG (FIG. 1; compare curves A and E).

The murG gene can be obtained from the pUG18 plasmid available from Prof. W. D. Demachie (Univ. of Edinburgh). The *E. coli* murG gene sequence is described by Mengin-Lecreulx, D. et al., in Nucleic Acids Res. 1990, 18, 2810 and Ikeda, M. et al., in Ibed. 1990, 18,4014. Gene amplification by polymerase chain reaction using the pUG18 plasmid as the template is performed. The pT7BlueT PCR cloning vector, which is available from Novagen, is used for this purpose. The DNA fragment that contains murG is cleaved from pT7BlueT plasmid by restriction enzymes Ndel and BamHI, and the fragment is purified by gel electrophoresis. The purified fragment is then inserted into the Ndel/BamHI cloning site of the pET15b expression vector, also available from Novagen.

The murG gene is subcloned from pET15b into a ET3a plasmid (Novagen). MurG is overexpressed in the IPTG-inducible BL21(DE3)pLysS strain (Novagen). See: Studier, F. W.; Rosenberg, A. H.; Dunn, J. J.; Dubendorff, J. W. Meth. Enzymol. 1990, 185, 60. Heat treating the overexpressing cell lysate prior to adding it to the substrate prevents the reaction from proceeding (See, FIG. 1; compare A and D). Hence, the reaction depends on the presence of active MurG. Furthermore, both the initial reaction rate and conversion to coupled product increases with the concentration of 9 (See, FIG. 1; compare A, B, and C).

Therefore, the synthetic substrate analog functions efficiently in a direct assay for MurG activity despite having a different, and dramatically shorter, lipid chain. This synthetic substrate can be used to evaluate enzyme activity in overexpressing cell lysates, following structural modifications to the murG gene which produce amino acid truncations, additions, deletions, substitutions, or other mutations. The synthetic substrate analog can also be used to assay for enzyme activity during purification, as well as for detailed mechanistic studies on wholly or partially purified enzyme. Thus, a high resolution structural analysis of MurG is now possible. In addition, by evaluating the ability of other synthetic substrates to compete with 9 for $^{14}$C-UDP-GlcNAc, it is possible to identify simpler acceptors for use in direct screens for MurG inhibition.

As a further illustration of the invention, the following examples are provided.

6. EXAMPLES

The following procedures are provided making specific reference to Scheme 2, above, and Methods 1–4, below.

6.1. Preparation of Compound 2

Compound 1 (482 mg, 1.022 mmol, Sigma) and 4-dimethylaminopyridine (10 mg, 0.080 mmol) are premixed, dried three times by azeotropic distillation with toluene, and then dissolved in 8 mL of tetrahydrofuran (THF). Trichloroethanol (0.23 mL, 2.405 mmol) is added to the reaction vessel followed by 1,3-dicyclohexylcarbodiimide (248 mg, 1.203 mmol). After stirring at room temperature for 4 h, the reaction solution is filtered through a cotton plug and rinsed with ethyl acetate (EtOAc). The filtrate is concentrated and purified by flash chromatography (15% EtOAc/CH$_2$Cl$_2$) to give 453 mg (80%) of a white powder. R$_f$ 0.39 (15% EtOAc/CH$_2$Cl$_2$); $^1$H NMR (CDCl$_3$, 270 MHz) δ7.43–7.25 (m, 10 H), 7.67 (d, J=6.0 Hz, 1 H), 5.59 (s, 1 H), 5.34 (d, J=3.2 Hz, 1 H), 4.98 (d, J=11.9 Hz, 1 H), 4.71–3.70 (m, 10 H), 2.04 (s, 3 H), 1.50 (d, J=7.0 Hz, 3 H); Mass spec. [M+H]$^+$, 603.5.

6.2. Preparation of Compound 3

Compound 2 (360 mg, 0.599 mmol) is dissolved in 30 mL of EtOAc, and 900 mg of 20% Pd-C is added. The reaction vessel is filled with hydrogen and stirred at room temperature. After 30 min, the catalyst is filtered off and washed with methanol. The filtrate is concentrated to give a fully hydrogenated product, which is used in the next reaction without further purification.

To a solution of the triol in 6 mL of DMF is added benzylaldehyde dimethyl acetal (0.9 mL, 6 mmol) and p-toluenesulfonic acid (11.4 mg, 0.06 mmol). The reaction mixture is stirred at room temperature for 10 h, neutralized with saturated NaHCO$_3$, extracted with CH$_2$Cl$_2$ (3×20 mL), dried over Na$_2$SO$_4$, filtered, concentrated, and purified by flash chromatography (90%/EtOAc/petroleum ether) to give 248 mg (81%) of a mixture of α, β anomers.

6.3. Preparation of Compound 4

Compound 3 (202 mg, 0.395 mmol) and 1H-tetrazole are premixed and dried by azeotropic distillation with toluene, then dissolved in 10 mL of CH$_2$Cl$_2$, and cooled to −30° C. To the solution is added dibenzyl N,N-diisopropylphosphamide (0.266 mL, 0.791 mmol). The mixture is stirred at room temperature for 1 h and cooled to −40° C., m-CPBA (560 mg, 2 mmol) is added, and the reaction is stirred for 30 min at 0° C. and then 30 min at room temperature. The mixture is diluted with CH$_2$Cl$_2$, washed with 10% aqueous Na$_2$SO$_3$, saturated NaHCO$_3$, and water; then dried over Na$_2$SO$_4$, filtered, concentrated, and purified by flash chromatography (65% EtOAc/petroleum ether) to give 200 mg (70%) of white solid. R$_f$ 0.24 (70% EtOAc/ petroleum ether); $^1$H NMR (CDCl$_3$, 270 MHz) δ 7.44–7.33 (m, 15 H), 7.20 (d, J=6.0 Hz, 1 H), 6.10 (m, 1 H), 5.56 (s, 1 H), 5.05 (m, 6 H), 4.61 (q, J=7.0 Hz, 2 H), 4.10–3.61 (m, 6 H), 1.86 (s, 3 H), 1.48 (d, J=7.0 Hz, 3 H).

6.4. Preparation of Compound 5

Zinc dust is added to a solution of compound 4 (58 mg, 0.0752 mmol) in 5 mL of 90% AcOH/H$_2$O. The mixture is stirred vigorously at room temperature. After 1 h, the catalyst is filtered off, the filtrate is concentrated and purified by flash chromatography (10% MeOH/CHCl$_3$, 0.1% AcOH) to give 44 mg (91%) of product. R$_f$ 0.19 (5% MeOH/CHCl$_3$, 0.1% AcOH); $^1$H NMR (CD$_3$OD, 500 MHz) δ 7.44–7.25 (m, 15 H), 6.11 (m, 1 H), 5.55 (s, 1 H), 5.02 (m, 4 H), 4.33 (q, J=7.0 Hz, 1 H), 3.96 (m, 1 H), 3.77 (m, 1 H), 3.73–3.66 (m, 4 H), 1.94 (s, 3 H), 1.32 (d, J=7.0 Hz, 3 H).

6.5. Preparation of Compound 6

Compound 5 (45 mg, 0.0704 mmol) and NH$_2$-L-Ala-γ-D-Glu(O-TMSE)-L-Lys(N-TEOC)-D-Ala-D-Ala-OCH$_3$ (35 mg, 0.0469 mmol) are premixed and dried by azeotropic distillation with toluene three times, then dissolved in 0.9 mL of DMF, then cooled to 0° C. Diisopropylethylamine (41 μL, 0.235 mmol) is added to reaction vessel followed by HOBt (12.7 mg, 0.0938 mmol) and pyBOP (49 mg, 0.0938 mmol). After stirring for 30 min at room temperature, the solution is diluted with 10 mL of EtOAc, washed with 0.01 N aqueous HCl, and water. The solution is then concentrated and purified by flash chromatography (5% MeOH/CHCl$_3$) to give 59 mg (92%) of compound 6. R$_f$ 0.16 (5% MeOH/ CHCl$_3$); $^1$H NMR (CD$_3$OD, 500 MHz) δ 7.50–7.30 (m, 15 H), 5.87 (m, 1 H), 5.63 (s, 1 H), 5.13 (m, 4 H), 4.41 (m, 1

H), 4.40 (m, 1 H), 4.36 (m, 1 H), 4.35 (m, 1 H), 4.30 (m, 1 H), 4.21 (m, 1 H), 4.19 (m, 2 H), 4.14 (m, 2 H), 4.13 (m, 1 H), 4.05 (m, 1 H), 3.84 (m, 1 H), 3.79 (m, 2 H), 3.76 (m, 1 H), 3.66 (s, 3 H), 3.09 (t, J=8.8 Hz, 2 H), 2.28 (t, J=8.8 Hz, 2 H), 2.18 (m, 1 H), 1.91 (m, 1 H), 1.86 (s, 3 H), 1.77 (m, 1 H), 1.67 (m, 1 H), 1.51 (m, 2 H), 1.43–1.35 (m, 18 H), 1.01–0.97 (m, 4 H), 0.05–0.02 (s, s, 18 H); Mass spec [M+H]$^+$ 1394.

6.6. Preparation of Compound 7

Compound 6 (15 mg, 0.011 mmol) is dissolved in 1 mL of MeOH and 20 mg of 20% Pd-C is added. The reaction vessel is filled with hydrogen and stirred at room temperature. A drop of diisopropylethylamine is added after 30 min, then the solution is diluted in 5 mL of MeOH and stirred for 20 min. The mixture is filtered, concentrated to give the hydrogenated, debenzylated product (7a), which is used in the next reaction without further purification. $R_f$ 0.28 (CHCl$_3$:MeOH:H$_2$O=3:2:0.5).

Citronellol phosphate (diisopropylethylammonium, 18 mg, 0.053 mmol) is dried three times by azeotropic distillation with toluene, then dissolved in 1 mL of CH$_2$Cl$_2$. Diisopropylethylamine (18.5 μL, 0.106 mmol) is added. The solution is cooled to −20° C., and diphenylphosphorochloridate (11.5 μL, 0.080 mmol) is added. The reaction vessel is allowed to warm up to room temperature and stirred for 1 h at room temperature. After the addition of methanol (0.1 mL), the reaction is stirred for a further 1 h at room temperature, then the solvents are evaporated, and the residue is dried twice by azeotropic distillation with toluene and dissolved in 0.2 mL of DMF.

Compound 7a from above is dried three times by azeotropic distillation with toluene and dissolved in 0.1 mL of DMF. Diisopropylethylamine (3.9 μL, 0.022 mmol) is added. 0.1 mL of the citronellol diphenylpyrophosphate solution is transferred to the solution containing compound 7a. The reaction mixture is stirred for 48 h at room temperature, then loaded directly to a C18 reverse phase column (8 mm×80 mm, particle size 40 μm, pore size 60 Å, from J. T. Baker) and eluted with CH$_3$CN/H$_2$O (0, 5%, 10%, 15%, 20%, 25%, 30%, 35% of 10 mL each) with 0.1% triethylamine. The fractions containing the pure compound are combined and concentrated to give 4.6 mg (28%) of white powder. $R_f$ 0.36 (CHCl$_3$:MeOH:H$_2$O=3:2:0.5); $^1$H NMR (DMSO, 500 MHz) δ 8.36 (d, J=7.2 Hz, 1 H), 8.21 (d, J=8.0 Hz, 1 H), 8.19 (d, J=8.2 Hz, 1 H), 8.10 (d, J=6.0 Hz, 1 H), 7.32 (d, J=7.5 Hz, 1 H), 6.95 (t, J=5.0 Hz, 1 H), 5.26 (d, J=6.0 Hz, 1 H), 5.07 (t, J=7.0 Hz, 1 H), 4.30 (m, 1 H), 4.27 (m, 1 H), 4.23 (m, 1 H), 4.13 (m, 1 H), 4.12 (m, 2 H), 3.87 (m, 1 H), 3.77 (m, 2 H), 3.62 (m, 1 H), 3.60 (s, 3 H), 3.51 (m, 1 H), 3.33 (m, 1 H), 2.91 (m, 2 H), 2.17 (m, 2 H), 1.94 (m, 2 H), 1.91 (m, 1 H), 1.80 (s, 3 H), 1.62 (s, 3H), 1.58 (s, 3 H), 1.51 (m, 3 H) 1.50 (m, 1 H), 1.49 (m, 1 H), 1.35 (m, 2 H), 1.29 (d, J=7.2 Hz, 3 H), 1.27 (m, 2 H), 1.25 (d, J=6.8 Hz, 3 H), 1.24 (d, J=5.5 Hz, 3 H), 1.23 (m, 2 H), 1.19 (d, J=7.4 Hz, 3 H), 1.11 (m, 1 H), 0.84 (d, J=6.5 Hz, 3 H), 0.02–0.01 (s, s, 18 H); Mass spec. [M+H]$^+$ 1321.

6.7. Preparation of Compound 8

To a solution of compound 7 (5 mg, 0.0033 mmol) in 50 μL of DMF is added tetrabutylammonium fluoride (1 M in THF, 0.3 mL). The reaction mixture is stirred for 24 h at room temperature, then loaded directly to a C18 reverse phase column (8 mm×80 mm, particle size 40 μm, pore size 60 Å, from J. T. Baker) and eluted with CH$_3$CN/0.1% NH$_4$HCO$_3$ aqueous solution (0, 5%, 10%, 15%, 20%, 25%, 30% of 10 mL each). The fractions containing the pure compound are combined, concentrated, and lyophilized to remove salts. A white powder (2 mg, 57%) is obtained. $R_f$ 0.18 (CHCl$_3$:MeOH:H$_2$O=3:3:1); $^1$H NMR (CD$_3$OD, 500 MHz) δ 5.58 (m, 1 H), 5.11 (t, J=6.5 Hz, 1 H), 4.50–3.56 (m, 12 H), 2.94 (m, 2 H), 2.34 (m, 2 H), 2.10 (s, 3 H), 2.00 (m, 1 H), 1.98 (m, 2 H), 1.92 (m, 1 H), 1.74 (m, 2 H), 1.67 (s, 3 H), 1.62 (m, 1 H), 1.60 (s, 3 H), 1.50–1.39 (m, 12 H), 1.23 (m, 2 H), 0.93 (d, J=6.5 Hz, 3 H); Mass spec. [M+H]$^+$ 1062.

6.8. Preparation of Compound 9

To a solution of compound 8 (2 mg, 0.0019 mmol) in 0.1 mL of H$_2$O/dioxane(1:1) is added NaHCO$_3$ (3.2 mg, 0.038 mmol), followed by 6-((biotinoyl)amino)hexanoic acid succinimide ester (2 mg, 0.0044 mmol). The reaction mixture is stirred for 2 h at room temperature, then loaded directly to a C18 reverse phase column (8 mm×80 mm, particle size 40 μm, pore size 60 Å, from J. T. Baker) and eluted with CH$_3$CN/0.1% NH$_4$HCO$_3$ aqueous solution (0, 5%, 10%, 15%, 20%, 25%, 30% of 10 mL each). The fractions containing the pure compound are combined, concentrated, and lyophilized to remove salts. A white powder (2 mg, 76%) is obtained. $R_f$ 0.40 (CHCl$_3$:MeOH:H$_2$O=3:3:1); $^1$H NMR (CD$_3$OD, 500 MHz) δ 5.52 (d, J=4.5 Hz, 1 H), 5.12 (t, J=7.0 Hz, 1 H), 4.50 (m, 1 H), 4.39–4.19 (m, 8 H), 4.00–3.72 (m, 4 H), 3.51 (m, 1 H), 3.22 (m, 1 H), 3.18 (m, 2 H), 2.95 (dd, J=12.5, 5.0 Hz, 1 H), 2.71 (d, J=12.5 Hz, 1 H), 2.27 (m, 2 H), 2.02 (s, 3 H), 2.01 (m, 2 H), 1.85 (m, 2H), 1.67 (m, 2 H), 1.67 (s, 3 H), 1.62 (m, 1 H), 1.61 (s, 3 H), 1.53 (m, 2 H), 1.45–1.37 (m, 12 H), 1.38 (m, 1 H), 1.17 (m, 1 H), 0.94 (d, J=6.8 Hz, 3 H); Mass spec. [M+H]$^+$ 1402.

6.9. Preparation of Compound 10 (Method 1, below)

(R)-(+)-β-citronellol (330 mg, 2.111 mmol) is dried three times by azeotropic distillation with toluene, then dissolved in 21 mL of dry hexane. In another dry flask, phosphorus oxychloride (0.98 mL, 10.56 mmol) and triethylamine (1.47 mL, 10.56 mmol) are dissolved in 10 mL of dry hexane and stirred at room temperature. The citronellol solution is then added slowly (over 1 h) to the phosphorus oxychloride solution after which stirring is continued for 30 min. A mixture of 70 mL acetone/water/triethylamine (88:10:2) is added to the reaction, which is allowed to stir for 18 h at room temperature to convert citronellol phosphate dichloride to citronellol phosphate. The solvent is evaporated in vacuo to give an aqueous residue, which is loaded to a C18 reverse phase column (50 mm×12 cm, particle size 40 μm, pore size 60 Å, from J. T. Baker) and eluted with CH$_3$CN/H$_2$O (0, 10%, 20%, 30%, 40%, 50%, 60% of 100 mL each). The fractions containing the pure compound are combined and concentrated to give 566 mg (62%) of oily residue. $R_f$ 0.42 (CHCl$_3$:MeOH:H$_2$O=3:2:0.5); $^1$H NMR (CD$_3$OD, 500 MHz) δ 5.09 (t, J=5.0 Hz, 1 H), 3.90 (m, 2 H), 1.99 (m, 2 H), 1.67 (m, 1 H), 1.65 (s, 3 H), 1.62 (m, 1 H), 1.59 (s, 3 H), 1.41 (m, 1 H), 1.34 (m, 1 H), 1.16 (m, 1 H), 0.91 (d, J=6.5 Hz, 3 H); $^{13}$C NMR (CD$_3$OD, 500 MHz) δ 132.08, 125.96, 65.11, 39.00, 38.94, 30.45, 26.61, 26.10, 19.93, 17.92.

Method 1

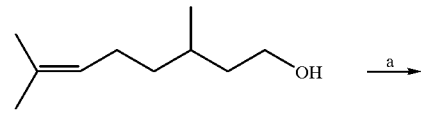

19
-continued

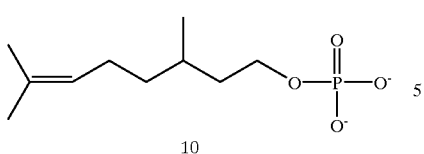

10

(a) 5 eq. POCl3, TEA, hexane, rt, 1 hr;
then add acetone/H2O/TEA (85:10:5), 10 hrs, 70%.

Method 2

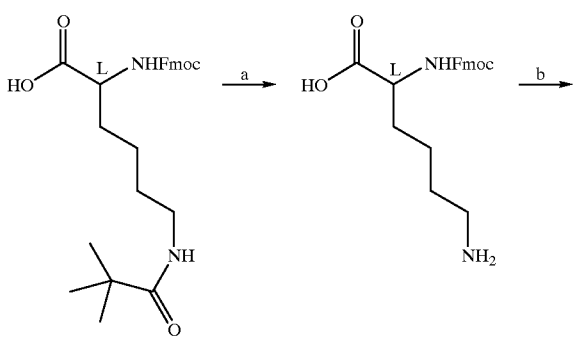

11

(a) 50% TFA/CH₂Cl₂, rt, 20 mins, 100%;
(b) 1.2 eq. 2-(Trimethylsilyl)ethyl p-nitrophenyl carbonate,
DIEA, DMF, 50° C., 2 hrs, 95%.

Method 3

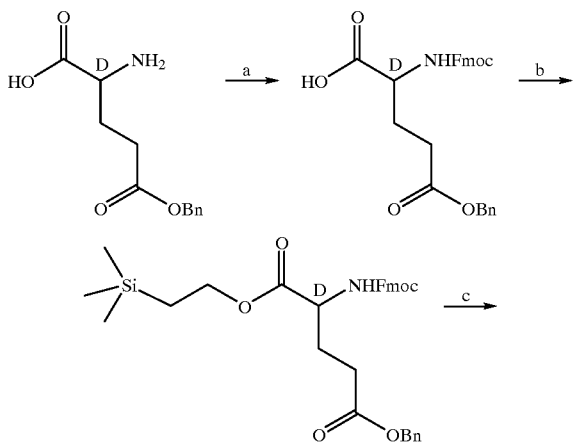

20
-continued

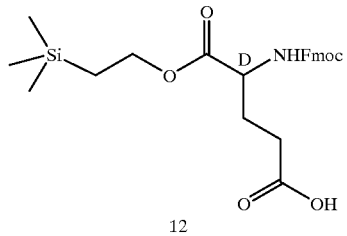

12

(a) 1.2 eq. 9-Fluorenylmethyl chloroformate, 3 eq.
NaHCO₃, H₂O/Dioxane(1:1), rt, 1 hr, 93%;
(b) 2 eq. trimethylsilyl ethanol, DCC/DMAP, EtOAc,
rt, 2 hrs, 82%;
(c) H2/Pd, MeOH, rt, 10 mins, 90%.

Method 4

Sasrin resin-OOC-D-Ala-Fmoc* —a, b→

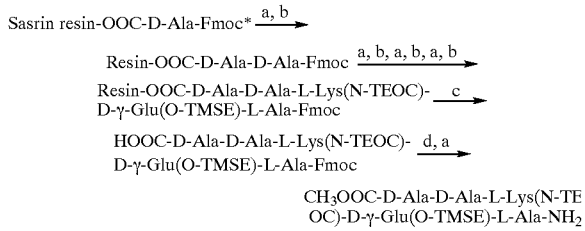

(a) 55% piperidine/NMP, rt, 30 mins;
(b) 4 eq. HO-D-Ala-Fmoc, HOBT/HBTU, DIEA, NMP, rt, 2 hrs;
identical coupling and deprotection conditions for HO-L-Lys(N-
TEOC)-Fmoc, HO-D-γ-Glu(O-TMSE), and HO-L-Ala-Fmoc
except for variations in the amount of amino acid used;
(c) 1% TFA/CH₂Cl₂, rt, 5 x 2 mins;
(d) KHCO₃, 50 eq. CH₃I, DMF, rt, 2 hrs overall yield 15%.
*Sasrin resin-OOC-D-Ala-Fmoc, an acid-sensitive resin, is available from
BACHEM Bioscience Inc..

6.10. Preparation of Compound 11 (Method 2)

To a solution of OH-L-Lys(N-BOC)-NHFmoc (607 mg, 1.295 mmol) in 10 mL of CH₂Cl₂ is added 10 mL of trifluoroacetic acid. The mixture is stirred for 20 min at room temperature, then concentrated and lyophilized. The residue is dissolved in 10 mL of DMF, then diisopropylethylamine (1.13 mL, 6.475 mmol) is added. 2-(Trimethylsilyl)ethyl p-nitrophenyl carbonate (440 mg, 1.554 mmol) is dissolved in 3 mL of DMF and transferred into the L-Lys solution. The mixture is stirred for 2 h at room temperature. The DMF solvent is evaporated in vacuo; the residue is purified by flash chromatography (EtOAc, followed by 10% MeOH/CHCl₃ with 0.1% AcOH) to give 635 mg (95%) of a white solid. $R_f$ 0.25 (10% MeOH/CHCl₃).

6.11. Preparation of Compound 12 (Method 3)

To a solution of D-Glu(benzyl) (1.046 g, 4.41 mmol) in 40 mL of water/dioxane (1:1) is added a solution of NaHCO₃ (1.1 g, 13.2 mmol) in 10 mL of water. The mixture is stirred for 20 min. Then, 9-Fluoenylmethyl chloroformate (1.37 g, 5.29 mmol) is dissolved in 10 mL of dioxane and added slowly (over 1 h) into the D-Glu solution after which stirring is continued for 10 min. The mixture is loaded directly to a silica gel column and eluted by 5% MeOH/CHCl₃ with 0.1% AcOH. Fractions containing product are combined, concentrated, and purified again by flash chromatography (EtOAc, followed by 5% MeOH/CHCl₃ with 0.1% AcOH) to give 1.88 g (93%) of a white powder. $R_f$ 0.27 (5% MeOH/CHCl₃ with 0.1% AcOH).

Fmoc-D-Glu(benzyl)-OH (350 mg, 0.762 mmol) and 4-dimethylaminopyridine (9.3 mg, 0.0762 mmol) are premixed and dried three times by azeotropic distillation with toluene, and dissolved in 8 mL of EtOAc. Trimethylsilyl ethanol (0.328 mL, 2.287 mmol) is added to the reaction vessel followed by 1,3-dicyclohexylcarbodiimide (314 mg, 1.525 mmol). After stirring the mixture for 2 h at room temperature, the reaction solution is filtered and washed with EtOAc. The filtration is concentrated and purified by flash chromatography (15% EtOAc/petroleum ether) to give 350 mg (82%) of a white powder. $R_f$ 0.33 (15% EtOAc/petroleum ether).

Fmoc-D-Glu(benzyl) 2-(trimethylsilyl) ethyl ester (270 mg, 0.483 mmol) is dissolved in 11 mL of methanol and 500 mg of 20% Pd-C is added. The reaction vessel is filled with hydrogen and stirred at room temperature. After 10 min, the mixture is filtered, concentrated, and purified by flash chromatography (10% MeOH/CHCl$_3$) to give 203 mg (90%) of a white powder. $R_f$ 0.43 (10% MeOH/CHCl$_3$).

6.12. Preparation of Compound 13 (Method 4)

Sasrin resin-OOC-D-Ala-NHFmoc (800 mg, 0.56 mmol) is put in reaction vessel and washed successively by the following solvents (20 mL each): CH$_2$Cl$_2$ (2×3 min), N-methylpyrrolidone (NMP, 2×3 min), 20% piperidine/NMP (30 min), NMP (2×3 min), 50% dioxane/water (2×5 min), NMP (3×5 min), CH$_2$Cl$_2$ (3×3 min), NMP (1×3 min). OH-D-Ala-NHFmoc (701 mg, 2.24 mmol), diisopropylethylamine (0.59 mL, 3.36 mmol), HOBt/HBTU (0.45 M in DMF, 2.5 mL), and 10 mL of NMP and added to the vessel and mixed thoroughly. The reaction vessel is shaken for 2 h at room temperature, then washed successively with the following solvents (20 mL each): NMP (5×8 min), i-PrOH (5×8 min), CH$_2$Cl$_2$ (4×3 min) and NMP (2×3 min).

The same procedure is used for the other 3 amino acids except that the Fmoc group is not cleaved for the last amino acid L-Ala-Fmoc.

After all of the amino acids are coupled, the pentapeptide is cleaved off of the resin by ishing with 1% TFA/CH$_2$Cl$_2$ (5×2 min, 15 mL each) with slight agitation. The cleavage solution is transferred via cannula into a vessel containing 2 mL of pyridine and 20 mL of methanol. The filtration is concentrated and purified three times by flash chromatography (5% MeOH/CHCl$_3$ with 1% AcOH) to give 300 mg (56%) of product. $R_f$ 0.34 (10% MeOH/CHCl$_3$).

KHCO$_3$ (28.4 mg, 0.284 mmol) is ground to a fine powder and mixed with Fmoc-L-Ala-D-γ-Glu(O-TMSE)-L-Lys(N-TEOC)-D-Ala-D-Ala-OH (135.4 mg, 0.142 mmol). The mixture is dissolved in 2 mL of DMF, CH$_3$I (0.44 mL, 7.1 mmol) is added. The mixture is stirred for 2 h at room temperature and purified by flash chromatography (90% EtOAc/petroleum ether) to give 47 mg (34%) of a white powder. $R_f$ 0.40 (100% EtOAc); $^1$H NMR (DMSO-d$_6$, 500 MHz) δ 8.24 (d, J=7.4 Hz, 1 H), 8.18 (d, J=7.2 Hz, 1 H), 8.17 (d, J=8.4 Hz, 1 H), 8.01 (d, J=7.1 Hz, 1 H), 7.89 (d, J=7.4 Hz, 2 H), 7.72 (dd, J=7.4, 7.4 Hz, 2 H), 7.47 (d, J=7.8 Hz, 1 H), 7.41 (dd, J=7.4, 7.4 Hz, 2 H), 7.32 (dd, J=7.4, 7.4 Hz, 2 H), 6.94 (t, J=5.2 Hz, 1 H), 4.29–4.12 (m, 8H), 4.11 (t, J=8.8 Hz, 2 H), 4.00 (t, J=8.2 Hz, 2 H), 3.59 (s, 3 H), 2.91 (m, 2 H), 2.17 (m, 2 H), 1.92 (m, 1 H), 1.79 (m, 1 H), 1.56 (m, 1 H), 1.48 (m, 1 H), 1.35 (m, 2 H), 1.28 (d, J=7.3 Hz, 3 H), 1.23 (m, 5 H), 1.19 (d, J=7.1 Hz, 3 H), 0.93 (t, J=8.8 Hz, 2 H), 0.89 (t, J=8.2 Hz, 2 H), 0.02–0.01 (s, s, 18 H); Mass spec [M+Na]$^+$ 992.

Fmoc-L-Ala-D-γ-Glu(O-TMSE)-L-Lys(N-TEOC)-D-Ala-D-Ala-OCH$_3$ (100 mg, 0.104 mmol) is dissolved in 2 mL of 20% piperidine/DMF and stirred for 30 min at room temperature. Solvent is evaporated in vacuo, and the residue is purified by flash chromatography (EtOAc, followed by 10% MeOH/CHCl$_3$) to give 60 mg (78%) of the desired product. $R_f$ 0.23 (10% MeOH/CHCl$_3$).

6.13. MurG Activity Assay Procedure 6.13.1. Protein Preparation

The wild type murG gene is cloned into the pET3a plasmid and transformed into the high-stringency expression host BL21(DE3)pLysS (Novagen). The lysogenized cells are grown at 37° C. in 2×YT media supplemented with 20 μg/mL ampicillin and 34 μg/mL chloramphenicol to an O.D.$_{600\ nm}$=0.7; overexpression of the murG protein is achieved by induction for 1.25 h with 1 mM IPTG. SDS/PAGE analysis shows production of a single new band migrating at ~38,000 MW. Several hundred aliquots of the induced cell culture are prepared by centrifuging 1.0 mL samples at 5000 rpm for 10 min at 4° C. The supernatant is removed, and the pellet frozen at −20° C. Frozen pellet stocks of non-transformed BL21(DE3)pLysS culture are also prepared as a negative control. Protein quantitation using a precipitated Lowry assay (Sigma) with a BSA reference on the entire pellet shows total protein concentration to be 11 and 17 μg/pellet for the BL21(DE3)pLysS and overexpressed cell cultures, respectively. Immediately prior to reactions, pellets are thawed on ice and resuspended in 100 μL 1× Rxn buffer.

6.13.2. Reaction Conditions

Biotinylated lipid substrate is aliquoted in autoclaved, sterile, deionized H$_2$O into 0.5 mL autoclaved Eppendorf tubes containing Rxn buffer (1×: 100 mM Tris-Cl pH 7.6, 1 mM MgCl$_2$). The ethanol is removed from an ethanol:water solution of $^{14}$C-UDP-GlcNAc (NEN Dupont) using an unheated SpeedVAC and then added to the substrate mixture (1.1×10$^5$ DPM; rxn concentration of 9.4 μM). Finally, 5 μL iced crude cell lysate containing 0.5–1.0 μg protein are added to a total volume of 20 μL. All reactions are performed at 24° C. Reactions are quenched by the addition of 10 μL 1% (w/v) SDS.

6.13.3. Transferase Activity Determination

A molar excess of biotin-binding TetraLink Tetrameric Avidin Resin (Promega) and deionized H$_2$O are added to each quenched reaction tube to a final volume of 350 μL. The suspension is incubated at room temperature for 10 min with frequent vortexing and transferred to an empty 1.5 mL microcolumn tube with a 30 μm frit (Bio-Rad). The resin is washed (5×0.5 mL) using deionized H$_2$O. Washed resin is transferred using 1.0 mL sterile, deionized H$_2$O to 10 mL Ecolite (ICN) and vortexed. Samples are counted immediately.

The results of various experiments are graphically depicted in FIG. 1.

6.14. Purification of Wild Type E. coli MurG

BL21(DE3)pLysS cells (Novagen) overexpressing wild type E. coli MurG from a pET3a vector (Novagen) are grown in 8 L 2XYT medium supplemented with 100 μg/mL ampicillin and 34 μg/mL chloramphenicol. When the OD$_{600\ nm}$ reached 0.6, IPTG is added to a final concentration of 1 mM. The induced cell culture is grown for another 3.5 hours and then the cells are spun down in 500 mL batches at 5000 rpm (Beckman RC5B centrifuge) for 10 minutes and the supernatant is decanted. Each cell pellet is resuspended in 5 mL 25 mM MES (pH 6.0), 4 mM DTT and 3% Triton X-100, and the suspensions are combined for a total of 80 mL, and then frozen at −70° C. The suspension is thawed at 4° C., and to it is added MgCl$_2$ to a final concentration of 5 mM and DNAse to a final concentration of 20 μg/mL. After shaking for 1 hour at 4° C., the debris is spun down at 15,000 rpm for 35 minutes. The supernatant is decanted, diluted 6-fold with Buffer A (25 mM MES pH 6.0, 4 mM DTT), and applied to a SP-Sepharose column (Pharmacia Biotech) equilibrated with Buffer A. After washing for 40 minutes with 40% Buffer B (20 mM Tris pH 8.0, 1M NaCl, 4 mM DTT)/Buffer A, the bound enzyme is eluted using a linear salt gradient starting with 40% Buffer B and ending with 100% Buffer B over 120 minutes. The eluted enzyme is concentrated to 7 mg/mL and applied to a Superdex 200 HR 10/30 column (Pharmacia Biotech) at a flow rate of 0.5 mL/min of TBSE buffer (100 mM NaCl, 20 mM Tris pH 8.0, 10 mM EDTA and 4 mM DTT). The protein eluted as a single, symmetric peak at an estimated molecular weight of 72 kD. The purity of the enzyme is estimated to be greater than 98% from a Coomassie Blue-stained SDS-polyacrylamide gel. The yield of purified enzyme is approximately 1.3 mg/L of bacterial culture. The purified enzyme is stored at 4° C., and is stable for at least one month.

The following examples are best related to FIGS. 2–8 of the specification.

6.15. Initial Rate Assays With Purified, Soluble Enzyme

The following solutions are prepared prior to the assays: 1) 177.3 $\mu$M [$^{14}$C]-UDP-GlcNAc in H$_2$O (0.05 mCi/mL); 2) 1.5 mM UDP-GlcNAc in H$_2$O; 3) biotinylated Lipid I analog (1b) at 0.5 $\mu$g/$\mu$L; 4) 10X reaction buffer containing 50 mM HEPES (pH 7.9) and 5 mM MgCl$_2$. The enzyme stock is prepared by diluting the purified enzyme with TBSE to a final concentration of 0.04 $\mu$g/$\mu$L in a 0.5 mL tube and storing at 4° C. for two days prior to running the assays.

Thirty reactions are prepared by individually mixing 2 $\mu$L of 10X reaction buffer with an appropriate amount of biotinylated Lipid I analog (1b), radioactive UDP-GlcNAc, nonradioactive UDP-GlcNAc, and H$_2$O to a final volume of 18 $\mu$l. The final concentrations for the Lipid I analog (1b) are 7 $\mu$M, 10 $\mu$M, 15 $\mu$M, 30 $\mu$M, 100 $\mu$M, and for UDP-GlcNAc 11 $\mu$M, 15 $\mu$M, 20 $\mu$M, 40 $\mu$M, 100 $\mu$M, 200 $\mu$M. Reactions are initiated by adding 2 $\mu$L of the enzyme stock and are run for 4 minutes at 24° C. Reactions are stopped by adding 10 $\mu$l of 1% (w/v) SDS.

Radiolabeled product is separated from radiolabeled starting material by incubating a 3-fold molar excess of biotin-binding TetraLink Tetrameric Avidin Resin (Promega) to each tube. Deionized H$_2$O is added to each tube to a final volume of approximately 250 $\mu$L and the suspension is transferred to a 1.0 $\mu$m pore size 96-well filter plate fitted to a vacuum-line fitted MultiScreen Assay System (Millipore). The resin is washed 15 times with 0.2 mL deionized H$_2$O. Washed resin is transferred to a scintillation vial containing 10 mL Ecolite and vortexed. Samples are counted immediately on a Beckman LS5000 scintillation counter.

6.16. IC$_{50}$ Measurements

The IC$_{50}$ assays are performed the same way as the initial rate assays except that the Lipid I analog (1b) and UDP-GlcNAc concentrations are fixed at 18 $\mu$M and 34.3 $\mu$M, respectively. Each set of assays is carried out at five or six different concentrations of one of the inhibitory compounds. The IC$_{50}$ is taken as the concentration at which the reaction rate (counts incorporated in a given time) decreased by 50%.

6.17. General Methods

All amino acids are purchased from BAChem. Unless otherwise stated, all chemicals are purchased from Aldrich or Sigma and used without further purification. Dichloromethane, toluene, benzene, pyridine, diisopropylethylamine and triethylamine are distilled from calcium hydride under dry argon. Diethyl ether and tetrahydrofuran are distilled from potassium benzophenone under dry argon. DMF, ethyl acetate and methanol are dried over activated molecular sieves.

Analytical thin layer chromatography (TLC) is performed on silica gel 60 F$_{254}$ plates (0.25 mm thickness) precoated with a fluorescent indicator. The developed plates are examined under short wave UV light and stained with anisaldehyde or Mo (Vaughn) stain. Flash chromatography is performed using silica gel 60 (230–400 mesh) from EM Science.

NMR spectra are recorded on a JOEL GSX-270 NMR spectrometer or a Varian Inova 500/VNMR spectrometer. Chemical shifts ($\delta$) are reported in parts per million (ppm) downfield from tetramethylsilane. Coupling constants (J) are reported in Hertz (Hz). Multiplicities are abbreviated as follows: singlet (s), doublet (d), triplet (t), quartet (q), multiplet (m), double of doubles (dd), apparent triplet (apt), broad singlet (bs), pentet (p), and octet (o).

High-resolution mass spectras (FAB) are obtained by Dr. Ron New at the University of California at Riverside Department of Chemistry Mass Spectrometry Facility. Low-resolution mass spectra (ESI) are obtained by Dr. Dorothy Little at the Princeton University Department of Chemistry.

6.17.1 Compound 3

To a solution of compound 2 (482 mg, 1.02 mmol; see, FIG. 7) and 4-dimethylaminopyridine (10 mg, 0.08 mmol) in 8 mL of THF is added trichloroethanol (0.23 mL, 2.40 mmol) followed by 1,3-dicyclohexylcarbodiimide (248 mg, 1.20 mmol). After stirring at room temperature for 4 hours, the reaction solution is filtered through cotton plug and the precipitate is rinsed with EtOAc. The filtrate is concentrated and purified by flash chromatography (15% EtOAc/CH$_2$Cl$_2$) to give 453 mg (80%) of 3 as a white powder. R$_f$ 0.39 (15% EtOAc/CH$_2$Cl$_2$); $^1$H NMR (CDCl$_3$, 500 MHz) $\delta$ 7.43–7.25 (m, 10 H), 7.07 (d, J=6.0 Hz, 1 H), 5.59 (s, 1 H), 5.34 (d, J=3.2 Hz, 1 H), 4.98 (d, J=11.9 Hz, 1 H), 4.68 (d, J=12.0 Hz, 1 H), 4.66 (q, J=7.0 Hz, 1 H), 4.60 (d, J=11.9 Hz, 1 H), 4.51 (d, J=12.0 Hz, 1 H), 4.21 (dd, J=10.5, 4.8 Hz, 1 H), 4.00 (m, 1 H), 3.85 (m, 2 H), 3.75 (m, 2 H), 2.04 (s, 3 H), 1.50 (d, J=7.0 Hz, 3 H); $^{13}$C NMR (CDCl$_3$, 500 MHz) $\delta$ 173.8, 170.9, 137.5, 137.4, 129.3, 128.6, 128.5, 128.1, 128.0, 126.1, 101.6, 97.5, 94.6, 83.4, 75.2, 75.1, 74.3, 70.5, 69.2, 63.1, 54.2, 23.4, 18.9; HRMS(FAB) calcd for C$_{27}$H$_{31}$NO$_8$Cl$_3$ [M+H$^+$]: 602.1115, found: 602.1130.

6.17.2. Compound 4

To a solution of compound 3 (360 mg, 0.60 mmol) in 30 mL of EtOAc is added 500 mg of 20% Pd-C. The reaction vessel is filled with hydrogen. After stirring at room temperature for 30 minutes, the suspension is filtered and the catalyst is rinsed with methanol. The filtrate is concentrated to give a clear oil which is used in the next reaction without further purification.

To a solution of this clear oil in 6 mL of DMF is added benzylaldehyde dimethyl acetal (0.9 mL, 6.0 mmol) followed by p-toluensulfonic acid (11.4 mg, 0.006 mmol). The reaction is stirred at room temperature for 10 hours and neutralized with saturated NaHCO$_3$. Then the mixture is extracted with CH$_2$Cl$_2$ (3×20 mL). The CH$_2$Cl$_2$ layers are combined, dried over anhydrous sodium sulfate, filtered, concentrated, and purified by flash chromatography (90% EtOAc/petroleum ether) to give 248 mg (81%) of 4 as a mixture of $\alpha$, $\beta$ anomers ($\alpha$:$\beta$=4:1). R$_f$ ($\alpha$ anomer) 0.33, R$_f$ ($\beta$ anomer) 0.28 (90% EtOAc/petroleum ether); $\alpha$ anomer $^1$H NMR (CDCl$_3$, 270 MHz) $\delta$ 7.50–7.35 (m, 5 H), 5.66 (bs, 1 H), 5.58 (s, 1 H), 5.02 (d, J=12.0 Hz, 1 H), 4.95 (m, 1 H), 4.67 (m, 1 H), 4.58 (d, J=12.0 Hz, 1 H), 4.27 (dd, J=10.0, 5.0 Hz, 1 H), 4.05 (m, 1 H), 2.06 (s, 3 H), 1.52 (d, J=7.0 Hz, 3 H); $^{13}$C NMR (CDCl$_3$, 270 MHz) $\delta$ 174.2, 171.9, 137.6, 129.2, 128.5, 126.2, 101.5, 94.7, 91.4, 83.5, 75.5, 75.0, 74.6, 69.2, 62.9, 54.9, 23.4, 18.9; HRMS(FAB) calcd for C$_{20}$H$_{25}$NO$_8$Cl$_3$ [M+H$^+$]; 512.0646, found: 512.0653.

6.17.3. Compound 5

Compound 4 (202 mg, 0.40 mmol) and 1H-tetrazole are premixed and co-evaporated with toluene and dissolved in 10 mL of CH$_2$Cl$_2$. The reaction solution is cooled to −30° C. and dibenzyl N,N-diisopropylphosphamide (0.27 mL, 0.79 mmol) is added. The reaction is warmed up to room temperature in 30 minutes and stirred for another hour. Then the reaction is cooled to −40° C. and m-CPBA (560 mg, 2 mmol) is added. After stirring for 30 minutes at 0° C. and another 30 minutes at room temperature, the reaction is diluted with 20 mL of $CH_2Cl_2$, extracted with 10% aqueous $Na_2SO_3$ (2×20 mL), saturated $NaHCO_3$ (2×20 mL), and water (2×20 mL). The $CH_2Cl_2$ layer is dried over anhydrous sodium sulfate, filtered, concentrated, and purified by flash chromatography (65% EtOAc/petroleum ether) to give 200 mg (70%) of 5 as a white solid. $R_f$ 0.24 (70% EtOAc/petroleum ether); $^1H$ NMR ($CDCl_3$, 500 MHz) δ 7.44–7.33 (m, 15 H), 7.20 (d, J=6.0 Hz, 1 H), 6.10 (m, 1 H), 5.56 (s, 1 H), 5.07 (m, 4 H), 5.02 (d, J=12.0 Hz, 1 H), 4.64 (q, J=7.0 Hz, 2 H), 4.59 (d, J=12.0 Hz, 1 H), 4.09 (m, 1 H), 4.03 (m, 1 H), 3.95 (m, 1 H), 3.83–3.68 (m, 3 H), 1.86 (s, 3 H), 1.48 (d, J=7.0 Hz, 3 H); $^{13}C$ NMR ($CDCl_3$, 500 MHz) δ 173.8, 171.2, 137.1, 129.4, 128.8, 128.5, 128.2, 128.0, 126.1, 101.7, 96.2, 96.1, 82.6, 75.3, 74.3, 74.2, 69.7, 68.6, 64.6, 54.2, 54.1, 23.0, 18.8; HRMS(FAB) calcd for $C_{34}H_{37}NO_{11}Cl_3PNa$ [M+Na$^+$]: 794.1068, found 794.1095.

6.17.4. Compound 6

To a solution of compound 5 (58 mg, 0.075 mmol) in 5 mL of 90% $AcOH/H_2O$ is added zinc dust (30 mg). The reaction is stirred vigorously at room temperature for 1 hour. The suspension is filtered and the precipitate is rinsed with methanol. The filtrate is concentrated and purified by flash chromatography (10% $MeOH/CHCl_3$/0.1% AcOH) to give 44 mg (91%) of 6 as a white solid. $R_f$ 0.19 (5% MeOH/$CHCl_3$, 0.1% AcOH); $^1H$ NMR ($CD_3OD$, 500 MHz) δ 7.44–7.25 (m, 15 H), 6.11 (m, 1 H), 5.55 (s, 1 H), 5.02 (m, 4 H), 4.33 (q, J=7.0 Hz, 1 H), 3.96 (m, 1 H), 3.77 (m, 1 H), 3.7–3.66 (m, 4 H), 1.94 (s, 3 H), 1.32 (d, J=7.0 Hz, 3 H); $^{13}C$ NMR ($CD_3OD$, 500 MHz) δ 181.2, 174.2, 139.0, 137.1, 130.0, 129.9, 129.3, 129.2, 127.3, 102.8, 97.4, 83.2, 78.3, 75.0, 71.2, 69.2, 66.4, 56.2, 56.1, 22.8, 19.7; HRMS(FAB) calcd for $C_{32}H_{36}NO_{11}PNa$ [M+N$^+$]: 664.1924, found 664.1938.

6.17.5. Compound 7

6.17.5.1. Fmoc-L-Lys(N-TEOC)-OH

To a solution of Fmoc-L-Lys(N-BOC)-OH (607 mg, 1.30 mmol) in 10 mL of $CH_2Cl_2$ is added 10 mL of trifluoroacetic acid. The mixture is stirred for 20 minutes at room temperature and concentrated. The residue is dissolved in 10 mL of DMF. Diisopropylethylamine (1.1 mL, 6.48 mmol) is added. 2-(Trimethylsilyl)ethyl p-nitrophenyl carbonate (440 mg, 1.55 mmol) is dissolved in 3 mL of DMF and transfered into the reaction solution. After stirring for 2 hours at room temperature, solvent is removed under vacuum. The residue is purified by flash chromatography (eluting first with EtOAc then with 10% $MeOH/CHCl_3$/0.1% AcOH) to give 635 mg (95%) of the desired product as a white solid. $R_f$ 0.54 (10% $MeOH/CHCl_3$).

6.17.5.2. Z-D-Glu(OH)-OTMSE

To a solution of Z-D-Glu(O-bzl)-OH (1.1 g, 3.0 mmol) and DMAP (37 mg, 0.3 mmol) in 30 mL of EtOAc is added DCC (0.7 g, 3.6 mmol) and 2-(Trimethylsilyl)ethanol (0.5 mL, 3.6 mmol). After stirring for 20 minutes at room temperature, the reaction is filtered. The filtrate is concentrated and purified by flash chromatography (15% EtOAc/petroleum ether) to give 1.3 g (91%) of Z-D-Glu(O-bzl)-OTMSE as a white solid. $R_f$ 0.30 (15% EtOAc/petroleum ether).

To a solution of Z-D-Glu(O-bzl)-OTMSE (1.2 g, 2.6 mmol) in 30 mL of MeOH is added 900 mg of 20% Pd-C. After stirring for 10 minutes at room temperature, the suspension is filtered. The filtrate is concentrated and dissolved in 20 mL of $H_2O$/dioxane (1:1). To the solution is added $NaHCO_3$ (0.44, 5.2 mmol). A solution of Cbz-succinimide (0.8 g, 3.1 mmol) in 5 mL of dioxane is added to the reaction over 30 minutes. Then 1 mL of AcOH is added. Solvent is removed under vacuum. The residue is purified by flash chromatography (eluting first with 10% EtOAc/$CH_2Cl_2$ then with 10% $MeOH/CHCl_3$/0.1% AcOH) to give 0.9 g (87%) of Z-D-Glu(OH)-OTMSE as a white solid. $R_f$ 0.49 (10% $MeOH/CHCl_3$); $^1H$ NMR ($CD_3OD$, 500 MHz) δ 7.24–7.15 (m, 5 H), 4.96 (d, J=3.0 Hz, 1 H), 4.10 (m, 4 H), 2.28 (t, J=7.6 Hz, 2 H), 2.02 (m, 1H), 1.80 (m, 1 H), 0.87 (t, J=8.6 Hz, 2 H), −0.08 (s, 9 H); $^{13}C$ NMR ($CD_3OD$, 500 MHz) δ 176.3, 173.9, 158.6, 138.2, 129.5, 129.1, 128.9, 67.7, 64.7, 55.0, 31.2, 27.8, 18.2, −1.3;

Peptide 7 is synthesized by standard HOBt/HBTU method with Fmoc protected amino acids. $R_f$ 0.29 (10% $MeOH/CHCl_3$); $^1H$ NMR (DMSO, 500 MHz) δ0 8.15 (d, J=5.0 Hz, 1 H), 8.14 (d, J=5.0 Hz, 1 H), 8.10 (d, J=8.0 Hz, 1 H), 8.02 (d, J=5.0 Hz, 1 H), 6.92 (t, J=5.0 Hz, 1 H), 4.30 (m, 1 H), 4.19 (m, 2 H), 4.17–4.07 (m, 5 H), 4.00 (t, J=8.5 Hz, 2 H), 3.31 (q, J=8.5 Hz, 1 H), 2.92 (m, 2 H), 2.18 (m, 2 H), 1.95 (m, 1 H), 1.80 (m, 1 H), 1.57 (m, 1 H), 1.48 (m, 1 H), 1.36 (m, 2 H), 1.29 (d, J=8.5 Hz, 3 H), 1.25 (m, 2 H), 1.20 (d, J=8.5 Hz, 3 H), 1.13 (d, J=8.5 Hz, 3 H), 0.92 (m, 6 H), 0.02–0.00 (3s, 27 H); $^{13}C$ NMR (DMSO, 500 MHz) δ 175.8, 172.3, 172.0, 171.8, 171.5, 171.4, 156.2, 62.6, 62.4, 61.2, 52.9, 51.3, 50.1, 47.7, 47.6, 31.4, 31.2, 29.2, 27.2, 22.6, 21.4, 18.0, 17.4, 16.9, 16.8, 16.7, −1.4, −1.5, −1.6; HRMS (FAB) calcd for $C_{36}H_{72}N_6O_{10}Si_3Na$ [M+Na$^+$]: 855.4515, found 855.4564.

6.17.6 Compound 8

To a solution of compound 6 (85 mg, 0.13 mmol) and $NH_2$-L-Ala-□-D-Glu(O-TMSE)-L-Lys(N-TEOC)-D-Ala-D-Ala-OTMSE (7) (153 mg, 0.18 mmol) in 1.5 mL of DMF is added diisopropylethylamine (116 μL, 0.66 mmol) followed by HOBt (27 mg, 0.20 mmol) and PyBOP (104 mg, 0.20 mmol). After stirring for 30 minutes at room temperature, the solution is diluted with 10 mL of EtOAc and washed with 0.01 N aqueous HCl (3×10 mL). The organic layer is concentrated, dried over anhydrous sodium sulfate, and purified by flash chromatography (5% MeOH/$CHCl_3$) to give 168 mg (87%) of 8 as a white solid. $R_f$ 0.24 (5% $MeOH/CHCl_3$); $^1H$ NMR ($CD_3OD$, 500 MHz) δ 7.52–7.37 (m, 15H), 5.88 (m, 1 H), 5.65 (s, 1 H), 5.13 (m, 4 H), 4.41 (m, 2 H), 4.35 (m, 3 H), 4.17 (m, 8 H), 4.06 (dd, J=9.5, 3.5 Hz, 1 H), 3.84 (m, 3 H), 3.77 (m, 1 H), 3.10 (m, 2 H), 2.29 (t, J=14.5 Hz, 2 H), 2.19 (m, 1 H), 1.90 (m, 1 H), 1.88 (s, 3 H), 1.77 (m, 1 H), 1.67 (m, 1 H), 1.51 (m, 2 H), 1.43–1.35 (m, 14 H), 1.01–0.97 (m, 6 H), 0.06–0.04 (3s, 27 H); $^{13}C$ NMR ($CDCl_3$, 500 MHz) δ 173.9, 172.8, 172.4, 171.8, 171.3, 157.1, 137.1, 135.5, 135.4, 129.2, 129.0, 128.9, 128.7, 128.4, 128.1, 126.1, 101.6, 97.1, 82.5, 81.0, 78.2, 76.7, 70.0, 69.6, 68.4, 64.8, 64.1, 63.8, 63.0, 53.9, 53.3, 51.4, 50.0, 49.1, 48.4, 40.4, 31.6, 31.5, 29.6, 27.9, 23.1, 22.7, 19.6, 18.0, 17.9, 17.8, 17.5, 17.4, −1.3, −1.4, −1.5; HRMS (FAB) calcd for $C_{68}H_{106}N_7O_{20}PSi_3Na$ [M+Na$^+$]: 1478.6436, found: 1478.6417.

6.17.7 Compound 9

To a solution of compound 8 (87 mg, 0.06 mmol) in 5 mL of MeOH is added 20 mg of 20% Pd-C. The reaction vessel is filled with hydrogen and stirred at room temperature. 1 mL of pyridine is added for 30 minutes. The solution is diluted with 15 mL of MeOH and stirred for 30 minutes. The catalyst is filtered off. The filtrate is concentrated to give product 9a which is used in the next reaction without further purification. $R_f$ 0.28 ($CHCl_3$:MEOH:$H_2O$=3:2:0.5).

Citronellol phosphate (25 mg, 0.11 mmol) [Ref: Warren, C. D., Jeanloz, R. W., *Biochem*, 14, 412–419, 1975] is coevaporated with toluene (3×1 mL) and dissolved in 2 mL of $CH_2Cl_2$. Diisopropylethylamine (92 μL, 0.53 mmol) is added. The solution is cooled to −20° C. and diphenylphosphorochloridate (26 μL, 0.13 mmol) is added. The reaction is allowed to warm up to room temperature in 10 minutes and stirred at room temperature. After 1 hour, methanol (1 mL) is added and the reaction is stirred for another hour at room temperature. Solvent is removed under vacuum. The residue is coevaporated with toluene (3×1 mL) and dissolved in 0.5 mL of $CH_2Cl_2$.

Compound 9a (58 mg, 0.04 mmol) is coevaporated with toluene (3×1 mL) and dissolved in 1 mL of $CH_2Cl_2$. 0.4 mL of citronellol diphenylpyrophosphate solution is added to the reaction followed by pyridine (20 μL, 0.24 mmol). The reaction is stirred at room temperature for 18 hours. Solvent is removed under vacuum and the residue is loaded to a C18 reverse phase column (8 mm×80 mm, particle size 40 μm, pore size 60 A, from J. T. Baker) and eluted with $CH_3CN$/0.1% $NH_4HCO_3$ aqueous solution (0, 5%, 10%, 15%, 20%, 25%, 30%, 35% of 10 mL each). The fractions containing desired product are combined and concentrated to give 34 mg (68%) of 9 as a white powder. $R_f$ 0.21 ($CHCl_3$:MeOH:$H_2O$=4.5:1.5:0.2). This product is used in the next reaction without further purification. ESI-MS calcd for $C_{57}H_{109}N_7O_{23}P_2Si_3Na$ [M+Na$^+$]: 1429, found: 1429.

6.17.8 Compound 1a

To a solution of compound 9 (43 mg, 0.023 mmol) in 0.7 mL of DMF is added tetrabutylammonium fluoride (1 M in THF, 0.7 mL). The reaction is stirred at room temperature for 24 hours. Solvent is removed under vacuum. The residue is loaded to a C18 reverse phase column (8 mm+80 mm, particle size 40 μm, pore size 60 A, from J. T. Baker), and eluted with $CH_3CN$/0.1% $NH_4HCO_3$ aqueous solution (0, 5%, 10%, 15%, 20%, 25%, 30% of 10 mL each). The fractions containing the desired product are combined and concentrated. The crude product is further purified on a diethylaminoethyl cellulose column (14 mm×80 mm, from Whatman Labsales, Inc.), eluted with 250 mM $NH_4HCO_3$, to give 24 mg of 1a (93%) as a white powder after lyophilization. $R_f$ 0.18 ($CHCl_3$:MeOH:$H_2O$=3:3:1); $^1$H NMR ($CD_3OD$, 500 MHz) δ 5.58 (m, 1 H), 5.11 (t, J=6.5 Hz, 1 H), 4.50–3.56 (m, 12 H), 2.94 (m, 2 H), 2.34 (m, 2 H), 2.10 (s, 3 H), 2.00 (m, 1 H), 1.98 (m, 2 H), 1.92 (m, 1 H), 1.74 (m, 2 H), 1.67 (s, 3 H), 1.62 (m, 1 H), 1.60 (s, 3 H), 1.50–1.39 (m, 12 H), 1.23 (m, 2 H), 0.93 (d, J=6.5 Hz, 3 H); $^{13}$C NMR ($D_2O$, 500 MHz) δ 178.2, 177.9, 176.7, 176.6, 176.5, 176.4, 176.3, 165.3, 135.5, 127.6, 97.0, 82.2, 80.3, 75.4, 74.1, 72.0, 71.9, 71.8, 70.4, 67.6, 62.7, 56.6, 55.8, 52.3, 51.9, 51.2, 41.5, 38.8, 34.0, 32.7, 31.0, 30.0, 28.6, 27.2, 27.1, 24.6, 24.4, 21.0, 19.2, 19.1, 18.8; ESI-MS calcd for $C_{41}H_{74}O_{21}N_7P_2$ [M+H$^+$]: 1062, found: 1062.

Compound 1b

To a solution of compound 1a (25 mg, 0.022 mmol) in 1.5 mL of $H_2O$/dioxane (1:1) is added $NaHCO_3$ (23 mg, 0.4 mmol) followed by 6-((biotinoyl)amino)hexanoic acid succinimide ester (12 mg, 0.027 mmol). The reaction is stirred at room temperature for 2 hours. Solvent is removed under vacuum. The residue is loaded on a diethylaminoethyl cellulose column (14 mm×80 mm, from Whatman Labsales, Inc.), eluted with 250 nm $NH_4HCO_3$ to give 16 mg (80%) of 1b as a white powder after lyophilization. $R_f$ 0.40 ($CHCl_3$:MeOH:$H_2O$=3:3:1); $^1$H NMR ($CD_3OD$, 500 MHz) δ 5.49 (dd, J=3.0, 7.3 Hz, 1 H), 5.11 (t, J=7.2 Hz, 1 H), 4.50 (dd, J=4.8, 7.8 Hz, 1 H), 4.37 (m, 2 H), 4.31 (dd, J=4.3, 7.8 Hz, 1 H), 4.29 (m, 1 H), 4.24 (m, 3H), 4.16 (d, J=10.4 Hz, 1 H), 4.02 (m, 1 H), 3.99 (m, 1 H), 3.90 (d, J=11.0 Hz, 1 H), 3.74 (m, 1 H), 3.70 (m, 1 H), 3.49 (dd, J=9.5, 9.5 Hz, 1 H), 3.21 (m, 1 H), 3.17 (m, 4 H), 2.94 (dd, J=4.8, 12.8 Hz, 1 H), 2.71 (d, J=12.8 Hz, 1 H), 2.31 (m, 1 H), 2.28 (m, 2 H), 2.25 (m, 1 H), 2.20 (m, 4 H), 2.02 (s, 3 H), 2.00 (m, 2 H), 1.86 (m, 2 H), 1.82 (m, 1 H), 1.73 (m, 4 H), 1.67 (s, 3 H), 1.63 (m, 5 H), 1.61 (s, 3 H), 1.52 (m, 4 H), 1.45 (m, 2 H), 1.44 (d, J=7.3 Hz, 3 H), 1.43 (d, J=6.2 Hz, 3 H), 1.41 (m, 2 H), 1.38 (d, J=7.3 Hz, 3 H), 1.37 (d, J=7.2 Hz, 3 H), 1.35 (m, 2 H), 1.17 (m, 1 H), 0.93 (d, J=6.7 Hz, 3 H); $^{13}$C NMR ($CD_3OD$, 500 MHz) δ 177.2, 176.5, 176.2, 176.1, 176.0, 175.6, 174.7, 174.6, 174.5, 174.2, 166.3, 132.1, 126.2, 96.4, 81.3, 78.8, 75.2, 71.0, 65.7, 63.6, 63.0, 61.8, 57.2, 55.7, 55.0, 54.2, 50.9, 50.7, 50.4, 41.2, 40.4, 40.2, 39.1, 39.0, 38.6, 37.2, 37.0, 33.0, 32.5, 30.6, 30.3, 30.2, 30.0, 29.6, 27.7, 27.1, 26.9, 26.7, 26.1, 24.5, 23.5, 20.0, 19.5, 18.4, 18.3, 18.0, 17.9; HRMS(FAB) calcd for $C_{57}H_{95}N_{10}O_{24}P_2SNa$ [M−3H$^+$+2Na$^+$]: 1443.5512, found: 1443.5494.

6.17.10 Compound 10

Compound 10 is made following the same scheme as 1a except that in step e, intermediate 6 is coupled to dipeptide $CH_3NH$-D-γ-Glu(O-TMSE)-L-Ala-$NH_2$ instead of to 7. $R_f$ 0.41 ($CHCl_3$:MeOH:$H_2O$=3:3:1); $^1$H NMR ($CD_3OD$, 500 MHz) δ 5.49 (dd, J=7.0 Hz, 1 H), 5.11 (t, J=6.6 Hz, 1 H), 4.33 (q, J=7.0 Hz, 1 H), 4.27 (q, J=7.0 Hz, 1 H), 4.24 (dd, J=3.8, 7.6 Hz, 1 H), 4.16 (m, 1 H), 4.04 (m, 2 H), 4.00 (m, 1 H), 3.90 (dd, J=1.8, 11.8 Hz, 1 H), 3.75 (dd, J=9.6, 9.6 Hz, 1 H), 3.70 (dd, J=5.7, 11.8 Hz, 1 H), 3.48 (dd, J=9.6, 9.6 Hz, 1 H), 2.64 (s, 3 H), 2.18 (m, 2 H), 2.16 (m, 1 H), 2.02 (s, 3 H), 1.98 (m, 2 H), 1.92 (m, 1 H), 1.72 (m, 1 H), 1.67 (s, 3H), 1.62 (m, 1 H), 1.61 (s, 3 H), 1.47 (m, 1 H), 1.43 (d, d, J=7.0 Hz, 6 H), 1.37 (m, 1 H), 1.18 (m, 1 H), 0.94 (d, J=6.6 Hz, 3 H); $^{13}$C NMR ($CD_3OD$, 500 MHz) δ 177.2, 176.1, 176.0, 174.4, 174.2, 132.0, 126.1, 96.3, 81.1, 78.9, 75.2, 70.8, 65.7, 63.0, 55.1, 54.9, 51.0, 39.1, 38.6, 33.3, 30.6, 30.1, 26.7, 26.5, 26.1, 23.4, 19.9, 19.5, 18.2, 17.9; HRMS(FAB) calcd for $C_{30}H_{53}N_4O_{17}P_2$ [M−H$^+$]: 803.2881, found: 803.2861.

6.17.11 Compound 11a

Compound 11a is made following the same scheme as 1a except that in step e, compound 6 is coupled to TEOC-$NHCH_2CH_2NH_2$ instead of to 7. The sily protecting group is cleaved using TBAF, the same as in making 1a. $R_f$ 0.20 ($CHCl_3$:MeOH:$H_2O$=3:2:0.5); $^1$H NMR ($CD_3OD$, 500 MHz) δ 5.58 (bs, 1 H), 5.11 (t, J=7.0 Hz, 1 H), 4.30 (q, J=6.7 Hz, 1 H), 4.21 (m, 1 H), 4.04 (m, 3 H), 3.72 (m, 1 H), 3.78 (m, 1 H), 3.73 (m, 1 H), 3.64 (m, 1 H), 3.50 (dd, J=9.4, 9.4 Hz, 1 H), 3.40 (m, 1 H), 3.13 (m, 2 H), 2.03 (s, 3 H), 2.00 (m, 2 H), 1.73 (m, 1 H), 1.67 (s, 3 H), 1.63 (m, 1 H), 1.61 (s, 3 H), 1.46 (m, 1 H), 1.39 (m, 1 H), 1.38 (d, J=6.7 Hz, 3 H), 1.18 (m, 1 H), 0.94 (d, J=6.7 Hz, 3 H); $^{13}$C NMR ($CD_3OD$, 500 MHz) δ (176.2, 173.6, 131.2, 125.2, 95.6, 80.7, 78.1, 74.3, 70.3, 64.9, 62.0, 54.2, 39.7, 38.2, 37.8, 37.5, 29.8, 25.8, 25.2, 22.5, 19.1, 18.6, 17.0; HRMS(FAB) calcd for $C_{23}H_{43}N_3O_{13}P_2Na$ [M−2H$^+$+Na$^+$]: 654.2169, found 654.2199.

6.17.12 Compound 11b

Compound 11a (4 mg, 0.006 mmol) and 4-nitrophenyl acetate (1.2 mg, 0.007 mmol) is dissolved in 0.4 mL of DMF. Large amount of $KHCO_3$ is added to increase PH. Equal amount of 4-nitrophenyl acetate is added every 12 hours. After 3 days, the reaction is completed. The solvent is removed and the residue is loaded to a $C_{18}$ reverse phase column (8 mm×80 mm, particle size 40 μm, pore size 60 A, from J. T. Baker) and eluted with $CH_3CN$/0.1% $NH_4HCO_3$ aqueous solution (0, 5%, 10%, 15%, 20%, 25%, 30%, 35% of 10 mL each). The fractions containing desired product are combined and concentrated to give 3 mg (71%) of 11b as a white powder. $R_f$ 0.26 ($CHCl_3$:MeOH:$H_2O$=3:2:0.5); $^1$H NMR ($CD_3OD$, 500 MHz) δ 5.50 (bs, 1 H), 5.12 (t, J=7.0

Hz, 1 H), 4.22 (q, J=7.0 Hz, 1 H), 4.04 (m, 2 H), 4.00 (m, 1 H), 3.89 (d, J=12.2 Hz, 1 H), 3.72 (m, 2 H), 3.46 (dd, J=9.5, 9.5 Hz, 1 H), 3.36 (m, 2 H), 3.28 (m, 2 H), 2.04 (s, 3 H), 2.02 (m, 2 H), 1.98 (s, 3 H), 1.73 (m, 1 H), 1.68 (s, 3 H), 1.63 (m, 1 H), 1.62 (s, 3 H), 1.46 (m, 1 H), 1.40 (d, J=7.0 Hz, 3 H), 1.38 (m, 1 H), 1.18 (m, 1 H), 0.94 (d, J=6.7 Hz, 3 H); $^{13}$C NMR (CD$_3$OD, 500 MHz) δ 176.4, 174.5, 173.8, 132.0, 126.1, 96.4, 81.9, 79.2, 75.1, 71.0, 65.6, 62.9, 55.0, 40.2, 40.1, 39.0, 38.6, 30.6, 26.7, 26.0, 23.4, 22.8, 19.9, 19.5, 17.9; HRMS(FAB) calcd for $C_{25}H_{46}N_3O_{14}P_2$ [M-H$^+$]: 674.2455, found 674.2488.

6.17.13 Compound 11c

Compound 11c is made from 11a and 6-((biotinoyl)amino)hexanoic acid succinimide ester using the same chemistry described in step h (scheme II). $R_f$ 0.30 (CHCl$_3$:MeOH:H$_2$O=3:2:0.5); $^1$H NMR (CD$_3$OD, 500 MHz) δ 5.49 (dd, J=2.7, 7.0 Hz, 1 H), 5.12 (t, J=7.2 Hz, 1 H), 4.50 (dd, J=5.0, 7.5 Hz, 1 H), 4.32 (dd, J=4.4, 7.5 Hz, 1 H), 4.20 (q, J=6.7 Hz, 1 H), 4.16 (m, 1 H), 4.03 (m, 2 H), 3.98 (m, 1 H), 3.90 (d, J=12.0 Hz, 1 H), 3.71 (m, 1 H), 3.70 (m, 1 H), 3.45 (dd, J=9.4, 9.4 Hz, 1 H), 3.23 (m, 1 H), 3.18 (m, 6 H), 2.94 (dd, J=5.0, 12.8 Hz, 1 H), 2.72 (d, J=12.8 Hz, 1 H), 2.24 (t, J=7.6 Hz, 2 H), 2.21 (t, J=7.6 Hz, 2 H), 2.03 (s, 3 H), 2.00 (m, 2 H), 1.73 (m, 3 H), 1.68 (s, 3 H), 1.64 (m, 6 H), 1.62 (s, 3 H), 1.53 (m, 2 H), 1.45 (m, 3 H), 1.40 (d, J=6.7 Hz, 3 H), 1.36 (m, 3 H), 1.18 (m, 1 H), 0.94 (d, J=6.7 Hz, 3 H); $^{13}$C NMR (CD$_3$OD, 500 MHz) δ 176.5, 176.4, 176.1, 174.4, 166.3, 132.0, 126.1, 96.5, 81.9, 79.2, 75.2, 70.9, 65.7, 63.5, 62.9, 61.8, 57.1, 55.0, 41.2, 40.4, 40.1, 39.1, 39.0, 38.6, 37.2, 37.0, 30.6, 30.3, 30.0, 29.6, 27.8, 27.1, 26.8, 26.7, 26.1, 23.4, 20.0, 19.6, 18,0; HRMS(FAB) calcd for $C_{39}H_{69}N_6O_{16}P_2S$ [M-H$^+$]: 971.3966, found: 971.3948.

6.17.14 Compound 12a

The intermediate from hydrogenation of compound 8 is deprotected with TBAF using the same method for making 1a. $R_f$ 0.16 (CHCl$_3$:MeOH:H$_2$O=3:4:1.5); $^1$H NMR (CD$_3$OD, 500 MHz) δ 5.34 (dd, J=3.0, 7.0 Hz, 1 H), 4.24 (m, 3 H), 4.17 (dd, J=6.7, 6.7 Hz, 1 H), 4.08 (dd, J=4.6, 8.5 Hz, 1 H), 4.03 (q, J=7.0 Hz, 1 H), 3.93 (m, 1 H), 3.80 (m, 1 H), 3.75 (m, 1 H), 3.59 (dd, J=5.5, 11.6 Hz, 1 H), 3.56 (m, 1 H), 3.38 (dd, J=9.7, 9.7 Hz, 1 H), 2.82 (t, J=7.3 Hz, 2 H), 2.22 (m, 2 H), 2.15 (m, 1 H), 1.86 (s, 3 H), 1.70 (m, 4 H), 1.58 (m, 2 H), 1.40 (m, 1 H), 1.31 (m, 6 H), 1.25 (m, 6 H); $^{13}$C NMR (CD$_3$OD, 500 MHz) δ 179.4, 178.8, 178.0, 176.2, 175.9, 174.7, 174.0, 173.8, 95.3, 81.2, 78.7, 74.9, 71.2, 62.8, 55.5, 55.3, 55.0, 51.9, 51.1, 50.8, 40.5, 33.1, 32.5, 30.4, 28.4, 23.7, 23.4, 19.8, 19.4, 18.4, 18.0; HRMS(FAB) calcd for $C_{31}H_{53}N_7O_{18}P$ [M-H$^+$]: 842.3185, found: 842.3212.

Compound 12b

Compound 12b is made from 12a and 6-((biotinoyl)amino)hexanoic acid succinimide ester using the same chemistry described in step h (scheme II). $R_f$ 0.27 (CHCl$_3$:MeOH:H$_2$O=3:4:1.5); $^1$H NMR (CD$_3$OD, 500 MHz) δ 5.45 (dd, J=7.0, 3.0 Hz, 1 H), 4.51 (dd, J=5.0, 7.5 Hz, 1 H), 4.39 (m, 2 H), 4.32 (m, 2 H), 4.26 (m, 3 H), 4.12 (m, 1 H), 3.91 (m, 1 H), 3.86 (d, J=11.6 Hz, 1 H), 3.73 (dd, J=5.5, 11.6 Hz, 1 H), 3.69 (m, 1 H), 3.53 (m, 1 H), 3.22 (m, 1 H), 3.17 (m, 4 H), 2.94 (dd, J=5.0, 12.8 Hz, 1 H), 2.72 (d, J=12.8 Hz, 1 H), 2.30 (m, 4H), 2.21 (m, 4 H), 1.99 (s, 3 H), 1.89 (m, 1 H), 1.82 (m, 1 H), 1.74 (m, 2 H), 1.63 (m, 4 H), 1.53 (m, 4 H), 1.46 (nm, 2 H), 1.44 (m, 6 H), 1.39 (m, 6 H), 1.35 (m, 4 H); $^{13}$C NMR (CD$_3$OD, 500 MHz) δ 177.5, 177.4, 177.3, 176.5, 176.3, 174.8, 174.7, 174.6, 174.3, 174.2, 166.0, 94.3, 80.6, 78.6, 73.2, 68.9, 62.8, 61.1, 60.9, 56.1, 55.0, 54.3, 54.2, 51.6, 50.4, 50.1, 40.4, 39.8, 39.6, 36.4, 36.2, 32.5, 31.4, 28.8, 28.7, 28.6, 28.5, 28.4, 26.2, 25.9, 25.8, 23.2, 22.7; HRMS(FAB) Calcd for $C_{47}H_{78}N_{10}O_{21}P_2S$ [M-H$^+$]: 1181.4801, found: 1181.4769.

6.17.16 Compound 13a

To a solution of compound 6 (12 mg, 0.019 mmol) in 1 mL of methanol is added 10 mg of pearlman's catalyst. The reaction vessel is filled with hydrogen. After stirring at room temperature for 30 min, a few drops of pyridine is added. The suspension is filtered after stirring for another 30 min. The filtration is concentrated to give a yellow oil which is purified on a diethylaminoethyl cellulose column (14 mm×80 mm, from Whatman Labsales, Inc.), eluted with 1M NH$_4$HCO$_3$, to give 7 mg (90%) of 13a as a white powder. $R_f$ 0.29 (CHCl$_3$:MeOH:H$_2$O=3:4:1.5); $^1$H NMR (CD$_3$OD, 500 MHz) δ 5.73 (d, J=7.3 Hz, 1 H), 4.72 (q, J=6.7 Hz, 1 H), 3.86 (m, 1 H), 3.84 (d, J=11.6 Hz, 1 H), 3.74 (m, 1 H), 3.70 (m, 1 H), 3.66 (dd, J=5.5, 11.6 Hz, 1 H), 3.45 (dd, J=9.8, 9.8 Hz, 1 H), 2.0 (s, 3 H), 1.83 (d, J=7.3 Hz, 3 H); $^{13}$C NMR (CD$_3$OD, 500 MHz) δ 180.4, 173.2, 93.7, 77.7, 77.4, 74.2, 71.8, 62.0, 54.5, 22.2, 19.2; HRMS(FAB) calcd for $C_{11}H_{19}NO_{11}P$ [M-H$^+$]: 372.0696, found: 372.0711.

6.17.17 Compound 13b

To a solution of 2 (20 mg, 0.042 mmol) in 1 mL of CH$_2$Cl$_2$ is added DIEA (16 μL, 0.924 mmol). The reaction vessel is cooled to −30° C., then MeOTf (5.2 μL, 0.046 mmol) is added. The reaction is complete after stirring at room temperature for 30 min. Saturated NaHCO$_3$ is added. The mixture is extracted with CH$_2$Cl$_2$ (3×5 mL). The organic layers are combined, dried over anhydrous sodium sulfate, filtered, concentrated and purified by flash chromatography (45% EtOAc/petroleum ether) to give 18 mg (87%) of product as a white powder. The following chemistry is the same as for 13a. $R_f$ 0.12 (CHCl$_3$:MeOH:H$_2$O=3:2:0.5); $^1$H NMR (CD$_3$OD, 500 MHz) δ 5.50 (dd, J=3.4, 7.3 Hz, 1 H), 4.58 (q, J=6.7 Hz, 1 H), 3.87 (m, 2 H), 3.84 (m, 1 H), 3.73 (3, 3 H), 3.62 (m, 2 H), 3.42 (dd, J=9.2, 9.2 Hz, 1 H), 2.00 (s, 3 H), 1.37 (d, J=7.0 Hz, 3 H); $^{13}$C NMR (CD$_3$OD, 500 MHz) δ 176.4, 173.8, 95.0, 80.7, 77.3, 74.8, 72.8, 62.9, 54.9, 52.6, 23.2, 19.4; ESI-MS calcd for $C_{12}H_{23}NO_{11}P$ [M+H$^+$]: 388, found: 388.

6.17.18 Compound 14

Compound 14a–c are made by the same approach as 1a, except by using R-OPO$_3$PO(OPh)$_2$ instead of (R)-(+)-β-citronellol-OPO$_3$PO(OPh)$_2$. ESI-MS for 14a $C_{32}H_{58}N_7O_{21}P_2$ [M+H$^+$]: 938; ESI-MS for 14b $C_{33}H_{60}N_7O_{21}P_2$ [M+H$^+$]: 952; ESI-MS for 14c $C_{34}H_{60}N_7O_{21}P_2$ [M+H$^+$]: 964.

6.17.19 Compound 15

To a microfuge tube containing 1 equivalent 1b (10 μg) and 3 equivalents $^{14}$C-UDP-GlcNAc in 100 μL HEPES reaction buffer (25 mM HEPES, pH 7.9, and 2.5 mM MgCl2) is added 1 μg purified MurG. The reaction is terminated after 30 minutes by heating MurG to 65° C. for five minutes. The reaction is evaluated by transferring a 10 μL aliquot to a tube containing a 3-fold molar excess of TetraLink Tetrameric Avidin Resin (based on the amount of 1b expected in one tenth of a volume of the reaction mixture), diluting with H2O, transferring the suspension to a 96 well filter plate, and ishing to remove unbound radioactivity as described in more detail under the experimental for the initial rate assays. The resin is then transferred to a scintillation vial containing Ecolite and counted. The conversion to disaccharide product 15 is estimated to be greater than 90% based on the counts incorporated into the resin. The mixture containing 15 is suitable for evaluating transglycosylase activity.

$^1$H NMR assignments are made from 1D and 2D spectra (COSY)

$^1$H NMR (CD$_3$OD, 500 MHz) δ ppm 5.09 (t, J=5.0 Hz, 1 H, H-7), 3.90 (m, 2 H, H-1), 1.99 (m, 2 H, H-6), 1.67 (m, 1

H, H-2), 1.65 (s, 3 H, H-9), 1.62 (m, 1 H, H-3), 1.59 (s, 3 H, H-10), 1.41 (m, 1 H, H-2'), 1.34 (m, 1 H, H-5), 1.16 (m, 1 H, H-5'), 0.91 (d, J=6.5 Hz, 3 H, H-4).

¹H NMR assignments are made from 1D and 2D spectra (COSY, ROESY)

¹H NMR (DMSO, 500 MHz) δ ppm 8.24 (d, J=7.5 Hz, 1 H, D-γ-Glu-N<u>H</u>), 8.18 (d, J=8.5 Hz, 1 H, D-Ala₂-N<u>H</u>), 8.17 (d, J=7.0 Hz, 1 H, D-Ala₁-N<u>H</u>), 8.01 (d, J=7.5 Hz, 1 H, L-Lys-N<u>H</u>), 7.47 (d, J=7.5 Hz, 1 H, L-Ala-N<u>H</u>), 6.94 (t, J=5.0 Hz, 1 H, L-Lys-N<u>H</u>COOR), 4.29 (m, 1 H, D-Ala₁-Hα), 4.24 (m, 1 H, D-Ala₂-Hα), 4.18 (m, 1 H, D-γ-Glu-Hα), 4.14 (m, 1 H, L-Lys-Hα), 4.12 (m, 1 H, L-Ala-Hα), 3.58 (s, 3 H, D-Ala₂-COOC<u>H</u>₃), 2.91 (m, 2 H, L-Lys-Hε), 2.17 (m, 2 H, D-γ-Glu-Hγ), 1.92 (m, 1 H, D-γ-Glu-Hβ), 1.79 (m, 1 H, D-γ-Glu-Hβ'), 1.56 (m, 1 H, L-Lys-Hβ), 1.48 (m, 1 H, L-Lys-Hβ'), 1.35 (m, 2 H, L-Lys-Hδ), 1.29 (d, J=7.0 Hz, 3 H, D-Ala₂-C<u>H</u>₃), 1.23 (d, J=6.5 Hz, 3 H, L-Ala-A<u>H</u>₃), 1.22 (m, 1 H, L-Lys-Hγ), 1.19 (m, 1 H, L-Lys-Hγ'), 1.19 (d, J=7.0 Hz, 3 H, D-Ala₁-C<u>H</u>₃), 0.01–0.00 (s, 9 H; s, 9 H, TMS-C<u>H</u>₃).

¹H NMR assignments are made from 1D and 2D spectra (COSY, NOESY)

¹H NMR (DMSO, 500 MHz) δ ppm 8.36 (d, J=7.2 Hz, 1 H, L-Lys-N<u>H</u>), 8.21 (d, J=8.0 Hz, 1 H, D-Ala₂-N<u>H</u>), 8.19 (d, J=8.2 Hz, 1 H, D-Ala₁-N<u>H</u>), 8.10 (d, J=6.0 Hz, 1 H, D-γ-Glu-N<u>H</u>), 7.32 (d, J=7.5 Hz, 1 H, L-Ala-N<u>H</u>), 6.95 (t, J=5.0 Hz, 1 H, L-Lys-N<u>H</u>COOR), 5.26 (d, J=6.0 Hz, 1 H, H-1'), 5.07 (t, J=7.0 Hz, 1 H, H-7), 4.30 (m, 1 H, L-Ala-Hα), 4.27 (m, 1 H, D-Ala₂-Hα), 4.23 (m, 1 H, D-Ala₁-Hα), 4.13 (m, 1 H, D-γ-Glu-Hα), 4.12 (m, 1 H, L-Lys-Hα), 4.12 (m, 1 H, H-7'), 3.87 (m, 1 H, H-2'), 3.77 (m, 2 H, H-1), 3.62 (m, 1 H, H-5'), 3.60 (s, 3 H, D-Ala₂-COOC<u>H</u>₃), 3.51 (m, 1 H, H-3'), 3.33 (m, 1 H, H-4'), 2.91 (m, 2 H, L-Lys-Hε), 2.17 (m, 2 H, D-γ-Glu-Hγ), 1.94 (m, 2 H, H-6), 1.91 (m, 1 H, D-γ-Glu-Hβ), 1.51 (m, 1 H, D-γ-Glu-Hβ), 1.80 (s, 3 H, NHCOC<u>H</u>₃-2'), 1.62 (s, 3 H, CH₃-9), 1.58 (s, 3 H, CH₃-10), 1.50 (m, 1 H, H-3), 1.51 (m, 1 H, L-Lys-Hβ), 1.49 (m, 1 H, L-Lys-Hβ), 1.35 (m, 2 H, L-Lys-Hδ), 1.51 (m, 1 H, H-2), 1.27 (m, 1 H, H-2), 1.29 (d, J=7.2 Hz, 3 H, D-Ala₁-C<u>H</u>₃), 1.19 (d, J=7.4 Hz, 3 H, D-Ala₂-C<u>H</u>₃), 1.24 (d, J=5.5 Hz, 3 H, C<u>H</u>₃-8'), 1.27 (m, 1 H, H-5), 1.11 (m, 1 H, H-5), 1.25 (d, J=6.8 Hz, 3 H, L-Ala-C<u>H</u>₃), 1.23 (m, 2 H, L-Lys-Hγ), 0.84 (d, J=6.5 Hz, 3 H, CH₃-4), 0.02–0.01 (s, 9 H; s, 9 H, TMS-C<u>H</u>₃).

¹H NMR are made from 1D and 2D spectra (COSY).

¹H NMR (CD₃OD, 500 MHz), δ ppm 5.58 (1 H, H-1'), 5.11 (t, J=6.5 Hz, 1 H, H-7), 4.50–4.00 (L-Ala-Hα, D-γ-Glu-Hα, L-Lys-Hα, D-Ala₁,₂-Hα, H-7'), 4.10 (m, 1 H, H-2'), 3.98 (m, 1 H, H-5'), 3.87 (m, 1 H, H-6'), 3.80 (m, 1 H, H-3'), 3.75 (m, 1 H, H-6'), 3.56 (m, 1 H, H-4'), 2.94 (m, 2 H, L-Lys-Hε), 2.34 (m, 2 H, D-γ-Glu-Hγ), 2.10 (s, 3 H, NHCOC<u>H</u>₃-2'), 2.00 (m, 1 H, D-γ-Glu-Hβ), 1.92 (m, 1 H, D-γ-Glu-Hβ), 1.98 (m, 2 H, H-6), 1.74 (m, 2 H, L-Lys-Hδ), 1.67 (s, 3 H, CH₃-9), 1.62 (m, 1 H, H-3), 1.60 (s, 3 H, CH₃-10), 1.50–1.39 (12 H, L-Ala-C<u>H</u>₃, D-Ala₁,₂-C<u>H</u>₃, C<u>H</u>₃-7'), 1.23 (m, 2 H, L-Lys-Hγ), 0.93 (d, J=6.5 Hz, 3 H, CH₃-4).

¹H NMR are made from 1D and 2D spectra (COSY).

¹H NMR (CD₃OD, 500 MHz) δ ppm 5.52 (d, J=4.5 Hz, 1 H, H-1'), 5.12 (t, J=7.0 Hz, 1 H, H-7), 4.50 (m, 1 H, H-b1), 4.39–4.19 (L-Ala-Hα, D-γ-Glu-Hα, L-Lys-Hα, D-Ala₁,₂-Hα, H-7'), 4.31 (m, 1 H, H-b2), 4.20 (m, 1 H, H-2'), 4.00 (m, 1 H, H-5'), 3.89 (m, 1 H, H-6'), 3.76 (m, 1 H, H-3'), 3.72 (m, 1 H, H-6'), 3.51 (m, 1 H, H-4'), 3.22 (m, 1 H, H-b4), 3.18 (m, 2 H, H-b9), 2.95 (dd, J=12.5, 5.0 Hz, 1 H, H-b3), 2.71 (d, J=12.5 Hz, 1 H, H-b3'), 2.27 (m, 2 H, D-γ-Glu-Hγ), 2.02 (s, 3 H, NHCOC<u>H</u>₃-2'), 2.01 (m, 2 H, H-6), 1.85 (m, 2 H, D-γ-Glu-Hβ), 1.67 (m, 2 H, H-b5), 1.67 (s, 3 H, C<u>H</u>₃-9), 1.61 (s, 3 H, C<u>H</u>₃-10), 1.62 (m, 1 H, H-3), 1.53 (m, 2 H, H-b10), 1.45–1.37 (12 H, L-Ala-C<u>H</u>₃, D-Ala₁,₂-C<u>H</u>₃, C<u>H</u>₃-8'), 1.38 (m, 1 H, H-5), 1.17 (m, 1 H, H-5), 0.94 (d, J=6.8 Hz, 3 H, C<u>H</u>₃-4).

The preceding examples are provided as a further illustration of the present invention. The specific embodiments described above are not to be construed to limit the invention in any way, which invention broadly encompasses such embodiments, as well as those embodiments that would be evident to those of ordinary skill upon consideration of the disclosure herein provided. The invention is limited solely by the claims, which follow.

What is claimed is:

1. A substance comprising the chemical moiety of the formula:

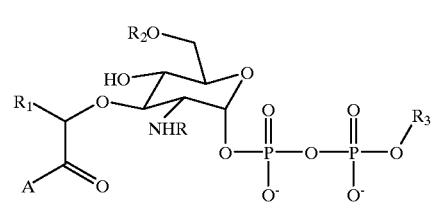

(I)

in which "R" is an acyl group comprising 2 or more carbon atoms, "R₁" is a substituted or unsubstituted alkyl group comprising 1 or more carbon atoms, "R₂" is a hydrogen or a substituted or unsubstituted alkyl group comprising 1 or more carbon atoms, "A" is a substituted or unsubstituted amino acid residue or a peptide comprising 2 or more substituted or unsubstituted amino acid residues, "R₃" comprises a substituted or unsubstituted alkyl group selected from the group consisting of moieties having 10 to 40 carbon atoms, pyrophosphate protecting groups and pharmaceutically acceptable salts thereof, said substance exhibiting a binding affinity for at least a soluble MurG enzyme.

2. The substance of claim 1 in which "A" or "R₃" is bound to a solid support.

3. The substance of claim 2 in which said solid support is an avidin or strepavidin coated resin and said "A" or "R₃" are conjugated to a biotin moiety.

4. The substance of claim 2 in which said biotin moiety is attached to "A" or "R₃" either directly or via a linker moiety.

5. A pharmaceutical composition comprising the substance of claim 1 and a pharmaceutically acceptable carrier.

6. The substance of claim 1 in which R₂ is H.

7. The substance of claim 1 in which R₁ is methyl.

8. The substance of claim 1 in which R is acetyl.

9. The substance of claim 1 in which R₃ is citronellyl.

10. The substance of claim 1 in which A comprises a biotin moiety.

* * * * *